(12) United States Patent
Sholev et al.

(10) Patent No.: US 12,161,542 B2
(45) Date of Patent: Dec. 10, 2024

(54) DEVICE ESPECIALLY USEFUL FOR HERNIA REPAIR SURGERIES AND METHODS THEREOF

(71) Applicant: Davol Inc., Warwick, RI (US)

(72) Inventors: Mordehai Sholev, Menashe (IL); Amir Szold, Tel Aviv-Jaffa (IL); Ibrahim Matter, Haifa (IL); Ziv Tamir, Moshav Lapid (IL)

(73) Assignee: Davol Inc., Warwick, RI (US)

( * ) Notice: Subject to any disclaimer, the term of this patent is extended or adjusted under 35 U.S.C. 154(b) by 787 days.

(21) Appl. No.: 17/131,505

(22) Filed: Dec. 22, 2020

(65) Prior Publication Data

US 2021/0169628 A1    Jun. 10, 2021

Related U.S. Application Data

(63) Continuation of application No. 15/825,806, filed on Nov. 29, 2017, now Pat. No. 10,898,309, which is a continuation of application No. 13/770,637, filed on Feb. 19, 2013, now Pat. No. 9,861,462, which is a continuation of application No. 12/516,373, filed as application No. PCT/IL2007/001463 on Nov. 27, 2007, now abandoned.

(60) Provisional application No. 60/861,095, filed on Nov. 27, 2006.

(51) Int. Cl.
*A61F 2/00*    (2006.01)
(52) U.S. Cl.
CPC .... *A61F 2/0063* (2013.01); *A61F 2002/0072* (2013.01)
(58) Field of Classification Search
CPC ........................ A61F 2/0063; A61B 17/22032

USPC ............................ 606/151; 623/23.74, 23.72
See application file for complete search history.

(56) References Cited

U.S. PATENT DOCUMENTS

| | | | |
|---|---|---|---|
| 460,940 A | 10/1891 | Baugii | |
| 3,857,395 A | 12/1974 | Johnson et al. | |
| 3,863,639 A * | 2/1975 | Kleaveland | A61B 17/0293 128/850 |

(Continued)

FOREIGN PATENT DOCUMENTS

| | | |
|---|---|---|
| EP | 0 557 963 A1 | 9/1993 |
| EP | 1 336 391 A1 | 8/2003 |

(Continued)

OTHER PUBLICATIONS

U.S. Appl. No. 16/194,747, filed Nov. 19, 2018, Felix et al.

(Continued)

*Primary Examiner* — Dianne Dornbusch
(74) *Attorney, Agent, or Firm* — Wolf, Greenfield & Sacks, P.C.

(57) ABSTRACT

An elongate open-bored applicator (EOBP) adapted to deploy a mesh comprising (a) at least one inflatable contour-balloon, (b) at least one inflatable dissection balloon. The inflatable contour-balloon and the inflatable dissection balloon are adjustable and located at the distal portion; and, (c) at least one actuating means located at the proximal portion. The actuating means is in communication with the inflatable contour-balloon and the inflatable dissection balloon. The actuating means is adapted to provide the inflatable contour-balloon and the inflatable dissection balloon with independent activation and/or de-activation.

20 Claims, 33 Drawing Sheets

(56) References Cited

U.S. PATENT DOCUMENTS

| | | | |
|---|---|---|---|
| 3,874,388 A | 4/1975 | King et al. | |
| 4,055,861 A | 11/1977 | Carpentier et al. | |
| 4,685,447 A | 8/1987 | Iversen et al. | |
| 4,769,038 A | 9/1988 | Bendavid et al. | |
| 4,823,815 A | 4/1989 | Watson et al. | |
| 5,011,481 A | 4/1991 | Myers et al. | |
| 5,116,357 A | 5/1992 | Eberlach | |
| 5,176,692 A | 1/1993 | Wilk | |
| 5,263,969 A | 11/1993 | Phillips | |
| 5,308,327 A * | 5/1994 | Heaven | A61B 17/00234 604/103.09 |
| 5,309,896 A * | 5/1994 | Moll | A61B 17/0218 604/908 |
| 5,333,624 A | 8/1994 | Tovey | |
| 5,350,388 A | 9/1994 | Epstein | |
| 5,361,752 A * | 11/1994 | Moll | A61B 17/0281 604/908 |
| 5,366,460 A | 11/1994 | Eberbach | |
| 5,370,650 A | 12/1994 | Tovey et al. | |
| 5,395,383 A | 3/1995 | Adams et al. | |
| 5,397,332 A | 3/1995 | Kammerer et al. | |
| 5,405,360 A | 4/1995 | Tovey | |
| 5,496,345 A | 3/1996 | Kieturakis et al. | |
| 5,527,264 A | 6/1996 | Moll et al. | |
| 5,575,759 A | 11/1996 | Moll et al. | |
| 5,607,443 A | 3/1997 | Kierturakis | |
| 5,695,498 A | 12/1997 | Tower | |
| 5,702,416 A | 12/1997 | Kierturakis | |
| 5,743,851 A | 4/1998 | Moll et al. | |
| 5,769,864 A | 6/1998 | Kugel | |
| 5,797,960 A | 8/1998 | Stevens et al. | |
| 5,824,082 A | 10/1998 | Brown | |
| 5,836,871 A | 11/1998 | Wallace et al. | |
| 5,836,961 A | 11/1998 | Kierturakis | |
| 5,871,498 A | 2/1999 | Jervis et al. | |
| 5,957,939 A | 9/1999 | Heaven et al. | |
| 6,168,608 B1 | 1/2001 | Echeverry et al. | |
| 6,171,318 B1 | 1/2001 | Kugel et al. | |
| 6,174,320 B1 | 1/2001 | Kugel et al. | |
| 6,176,863 B1 | 1/2001 | Kugel et al. | |
| 6,224,616 B1 | 5/2001 | Kugel | |
| 6,258,113 B1 | 7/2001 | Adams et al. | |
| 6,302,897 B1 | 10/2001 | Rousseau | |
| 6,312,442 B1 | 11/2001 | Kierturakis | |
| 6,358,266 B1 * | 3/2002 | Bonutti | A61M 29/02 604/103.08 |
| 6,361,543 B1 * | 3/2002 | Chin | A61B 17/0281 606/190 |
| 6,379,368 B1 | 4/2002 | Corcoran et al. | |
| 6,488,653 B1 | 12/2002 | Lombardo | |
| 6,551,241 B1 | 4/2003 | Schultz | |
| 6,565,590 B2 | 5/2003 | Kierturakis et al. | |
| 6,575,988 B2 | 6/2003 | Rousseau | |
| 6,638,292 B2 | 10/2003 | Adams | |
| 6,663,647 B2 | 12/2003 | Reiley et al. | |
| 6,679,900 B2 | 1/2004 | Kierturakis | |
| 6,685,714 B2 | 2/2004 | Rousseau | |
| 6,702,827 B1 | 3/2004 | Lund et al. | |
| 6,755,868 B2 | 6/2004 | Rousseau | |
| 6,866,676 B2 | 3/2005 | Kierturakis | |
| 6,913,614 B2 | 7/2005 | Marino et al. | |
| 7,048,698 B2 | 5/2006 | Whalen et al. | |
| 7,101,381 B2 | 9/2006 | Ford et al. | |
| 7,128,073 B1 | 10/2006 | van der Burg et al. | |
| 7,235,042 B2 | 6/2007 | Vanden Hoek et al. | |
| 7,273,489 B2 | 9/2007 | Boudjemline | |
| 7,544,213 B2 | 6/2009 | Adams | |
| 7,678,123 B2 | 3/2010 | Chanduszko | |
| 7,744,617 B2 | 6/2010 | Lunsford et al. | |
| 7,780,683 B2 | 8/2010 | Roue et al. | |
| 7,947,054 B2 | 5/2011 | Eldar et al. | |
| 8,007,502 B2 | 8/2011 | Chu et al. | |
| 8,016,851 B2 | 9/2011 | Dillon et al. | |
| 8,043,381 B2 | 10/2011 | Hestad et al. | |
| 8,372,112 B2 | 2/2013 | Christianson et al. | |
| 8,382,796 B2 | 2/2013 | Blaeser et al. | |
| 8,500,762 B2 | 8/2013 | Sholev et al. | |
| 8,920,370 B2 | 12/2014 | Sholev et al. | |
| 8,920,445 B2 | 12/2014 | Sholev | |
| 9,439,643 B2 | 9/2016 | Darois et al. | |
| 9,504,548 B2 | 11/2016 | Darois et al. | |
| 9,642,689 B2 | 5/2017 | Sholev et al. | |
| 9,687,332 B2 | 6/2017 | Sholev et al. | |
| 9,808,331 B2 | 11/2017 | Felix et al. | |
| 9,861,462 B2 | 1/2018 | Sholev et al. | |
| 9,993,324 B2 | 6/2018 | Sholev | |
| 10,166,093 B2 | 1/2019 | Felix et al. | |
| 10,548,703 B2 | 2/2020 | Darois et al. | |
| 10,751,156 B2 | 8/2020 | Sholev et al. | |
| 10,864,068 B2 | 12/2020 | Sholev | |
| 10,898,309 B2 | 1/2021 | Sholev et al. | |
| 10,905,537 B2 | 2/2021 | Felix et al. | |
| 2001/0053919 A1 | 12/2001 | Kieturakis et al. | |
| 2002/0133236 A1 | 9/2002 | Rousseau | |
| 2003/0004581 A1 | 1/2003 | Rousseau | |
| 2003/0187472 A1 | 10/2003 | Peartree et al. | |
| 2003/0236544 A1 | 12/2003 | Lunsford et al. | |
| 2004/0073257 A1 | 4/2004 | Spitz | |
| 2004/0087980 A1 | 5/2004 | Ford et al. | |
| 2004/0092970 A1 | 5/2004 | Xavier | |
| 2004/0097792 A1 | 5/2004 | Moll et al. | |
| 2004/0167557 A1 | 8/2004 | Kieturakis et al. | |
| 2004/0172048 A1 | 9/2004 | Browning | |
| 2004/0236363 A1 | 11/2004 | Kieturakis | |
| 2005/0033318 A1 | 2/2005 | Miller | |
| 2005/0049635 A1 | 3/2005 | Leiboff | |
| 2005/0059854 A1 | 3/2005 | Hoek et al. | |
| 2005/0171569 A1 | 8/2005 | Girard et al. | |
| 2005/0245960 A1 * | 11/2005 | Grundeman | A61B 17/0281 606/192 |
| 2006/0106418 A1 | 5/2006 | Seibold et al. | |
| 2006/0247586 A1 | 11/2006 | Voegele et al. | |
| 2007/0066980 A1 | 3/2007 | Leahy | |
| 2007/0078477 A1 | 4/2007 | Heneveld et al. | |
| 2007/0100369 A1 | 5/2007 | Cragg et al. | |
| 2007/0185506 A1 | 8/2007 | Jackson | |
| 2007/0260179 A1 | 11/2007 | Sholev et al. | |
| 2008/0033461 A1 | 2/2008 | Koeckerling et al. | |
| 2008/0065229 A1 * | 3/2008 | Adams | A61F 2/0063 623/23.75 |
| 2008/0147200 A1 | 6/2008 | Rousseau et al. | |
| 2008/0167729 A1 | 7/2008 | Nelson et al. | |
| 2008/0195121 A1 | 8/2008 | Eldar et al. | |
| 2009/0012350 A1 | 1/2009 | Tihon | |
| 2009/0082792 A1 | 3/2009 | Koyfman et al. | |
| 2009/0192605 A1 | 7/2009 | Gloss et al. | |
| 2009/0254103 A1 | 10/2009 | Deutsch | |
| 2009/0287046 A1 | 11/2009 | Yamatani | |
| 2010/0069947 A1 | 3/2010 | Sholev et al. | |
| 2010/0137999 A1 | 6/2010 | Shohat | |
| 2010/0292718 A1 | 11/2010 | Sholev et al. | |
| 2010/0318121 A1 | 12/2010 | Levin et al. | |
| 2011/0112560 A1 | 5/2011 | Sholev | |
| 2011/0295283 A1 | 12/2011 | Darois et al. | |
| 2012/0109179 A1 | 5/2012 | Murphy et al. | |
| 2013/0218179 A1 | 8/2013 | Sholev et al. | |
| 2013/0231526 A1 | 9/2013 | Felix et al. | |
| 2014/0051915 A1 | 2/2014 | Sholev et al. | |
| 2015/0196377 A1 | 7/2015 | Sholev et al. | |
| 2015/0202035 A1 | 7/2015 | Sholev | |
| 2017/0100229 A1 | 4/2017 | Darois et al. | |
| 2017/0290577 A1 | 10/2017 | Sholev et al. | |
| 2018/0092725 A1 | 4/2018 | Felix et al. | |
| 2018/0147040 A1 | 5/2018 | Sholev et al. | |
| 2018/0368962 A1 | 12/2018 | Sholev | |
| 2019/0151066 A1 | 5/2019 | Felix et al. | |
| 2021/0045862 A1 | 2/2021 | Sholev et al. | |

(56) References Cited

U.S. PATENT DOCUMENTS

| | | | |
|---|---|---|---|
| 2021/0128289 A1 | 5/2021 | Sholev | |
| 2021/0169629 A1 | 6/2021 | Felix et al. | |

FOREIGN PATENT DOCUMENTS

| | | |
|---|---|---|
| EP | 1 454 599 A2 | 9/2004 |
| GB | 2 397 239 A | 7/2004 |
| JP | 2000-501634 A | 2/2000 |
| JP | 2007-275203 A | 10/2007 |
| JP | 2008-520372 A | 6/2008 |
| WO | WO 95/30374 A1 | 11/1995 |
| WO | WO 96/00531 A1 | 1/1996 |
| WO | WO 97/21461 A1 | 6/1997 |
| WO | WO 2005/046511 A2 | 5/2005 |
| WO | WO 2006/040760 A2 | 4/2006 |
| WO | WO 2006/055823 A2 | 5/2006 |
| WO | WO 2007/030676 A2 | 3/2007 |
| WO | WO 2008/045635 A2 | 4/2008 |
| WO | WO 2009/050717 A2 | 4/2009 |

OTHER PUBLICATIONS

U.S. Appl. No. 15/825,806, filed Nov. 29, 2017, Sholev et al.
U.S. Appl. No. 16/934,939, filed Jul. 21, 2020, Sholev et al.
U.S. Appl. No. 17/131,937, filed Dec. 23, 2020, Felix et al.
U.S. Appl. No. 17/095,632, filed Nov. 11, 2020, Sholev.
PCT/IL2007/001463, Apr. 25, 2008, International Search Report.
PCT/IL2007/001463, Jun. 3, 2009, International Preliminary Report on Patentability.
International Search Report for Application No. PCT/IL2007/001463 mailed Apr. 25, 2008.
International Preliminary Report on Patentability for Application No. PCT/IL2007/001463 issued Jun. 3, 2009.

* cited by examiner

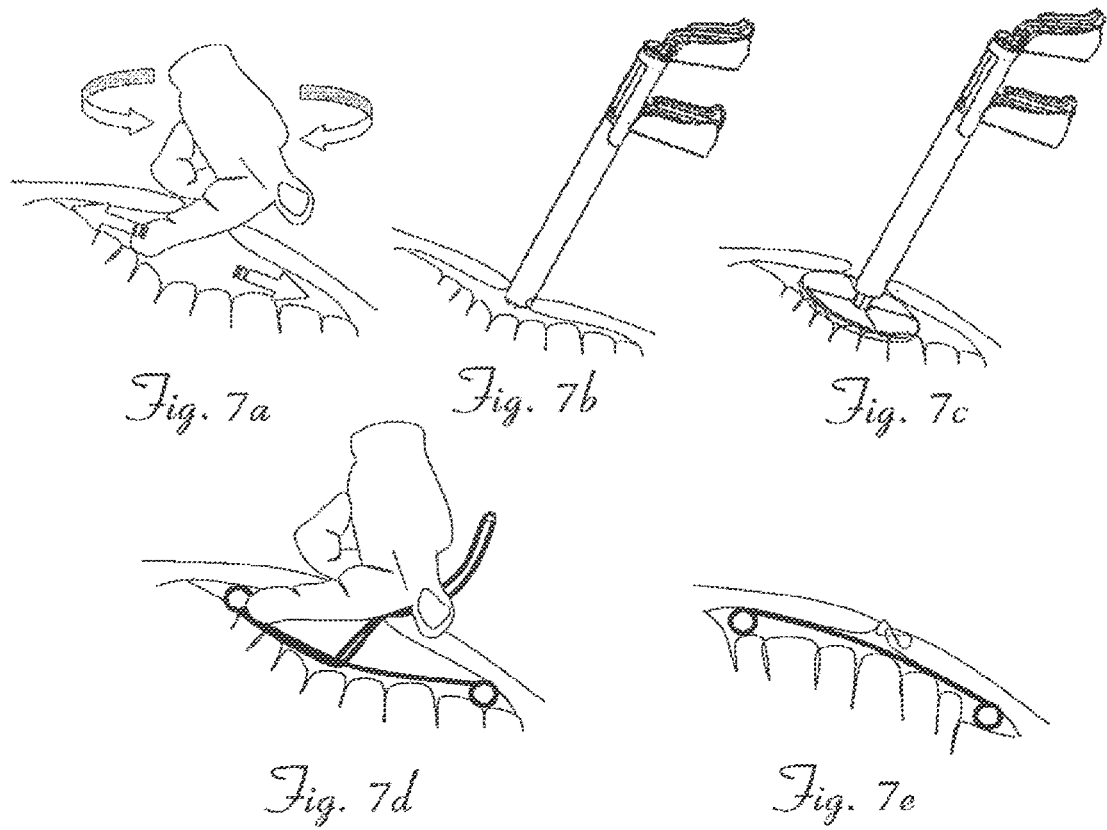

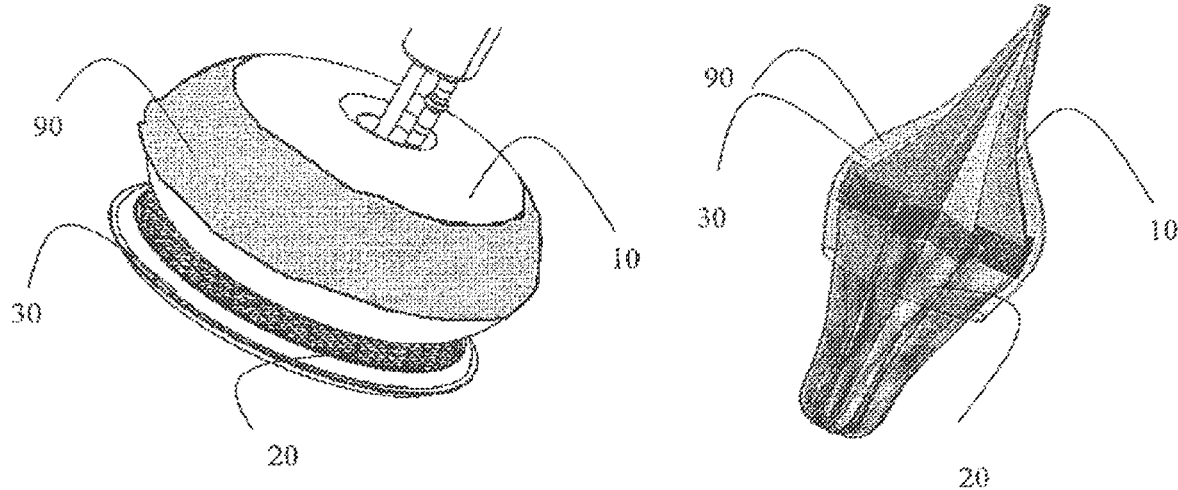
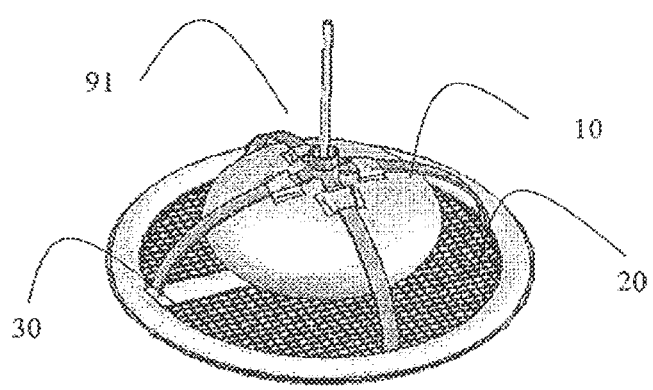

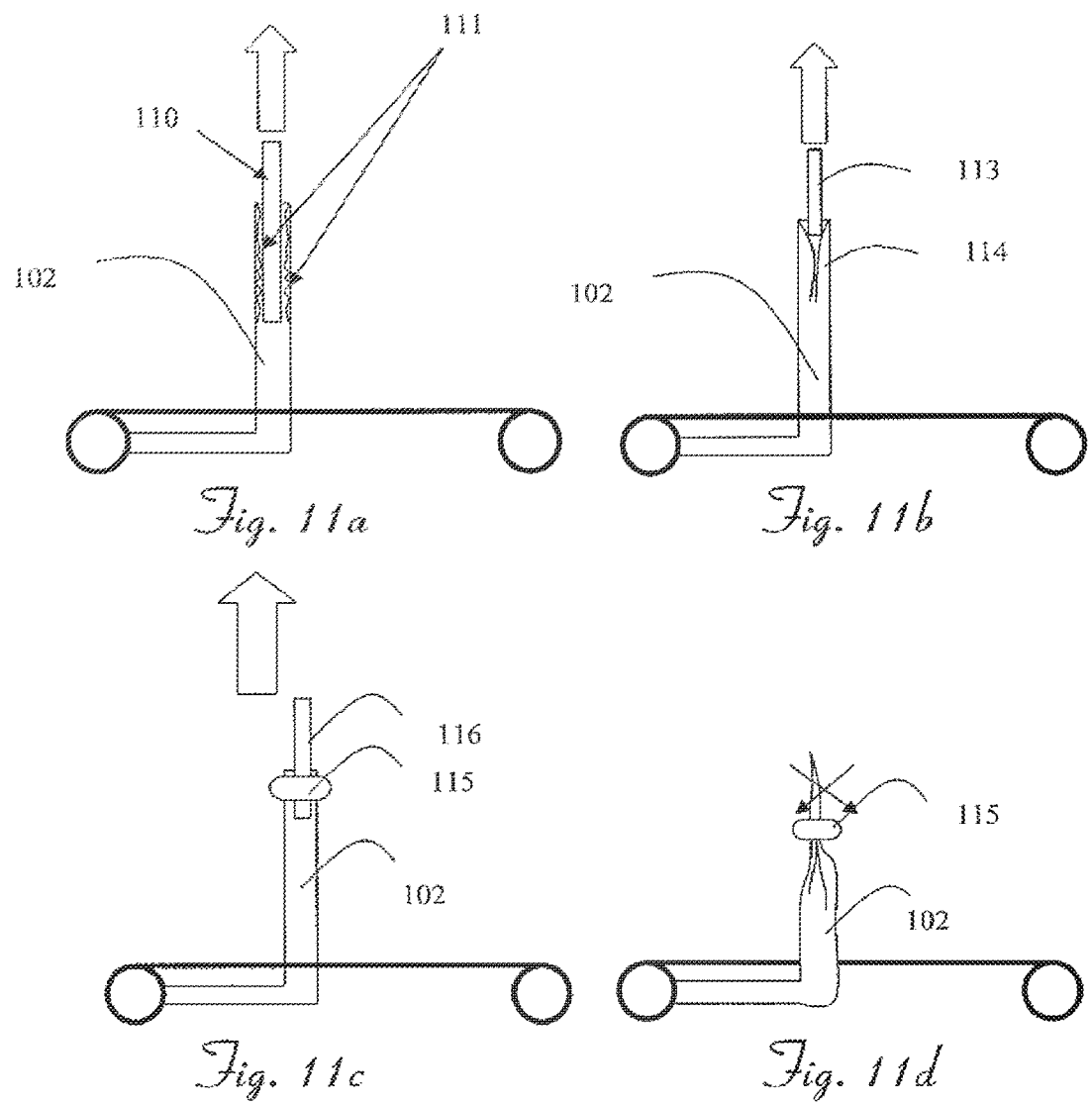

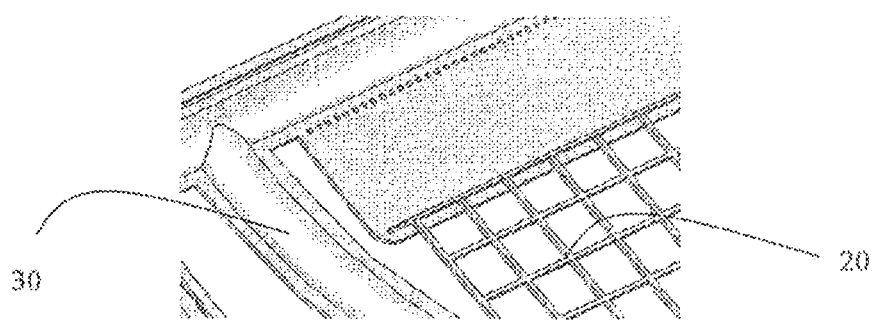
Figure 20b
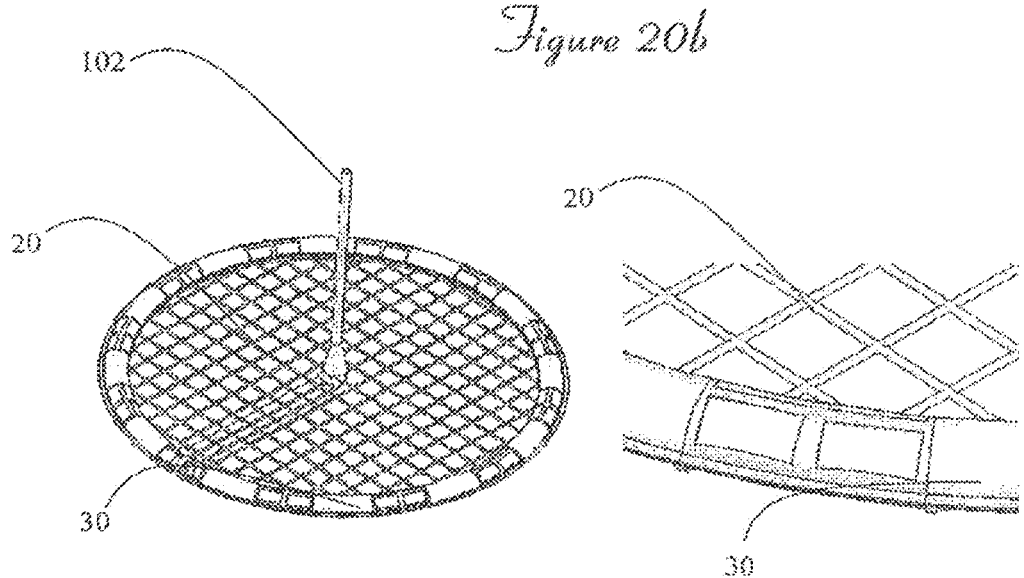
Figure 20d
Figure 20c

DEVICE ESPECIALLY USEFUL FOR HERNIA REPAIR SURGERIES AND METHODS THEREOF

RELATED CASE INFORMATION

This Application is a continuation of U.S. application Ser. No. 15/825,806, filed Nov. 29, 2017, now U.S. Pat. No. 10,898,309, which is a continuation of U.S. application Ser. No. 13/770,637, filed Feb. 19, 2013, now U.S. Pat. No. 9,861,462, which is a continuation of U.S. application Ser. No. 12/516,373, filed May 27, 2009, now abandoned, which is a national stage filing under 35 U.S.C. § 371 of International Patent Application Serial No. PCT/IL2007/001463, filed Nov. 27, 2007, which claims the benefit of U.S. Application Ser. No. 60/861,095, filed Nov. 27, 2006. The contents of these applications are incorporated herein by reference in their entirety.

FILED OF THE INVENTION

The present invention generally related to a device especially useful in hernia repair and a method of using the same.

BACKGROUND OF THE INVENTION

This invention generally relates to a device, especially useful for hernia repair surgery.

Hernia, denoted hereinafter for umbilical hernia, ventral hernia, postoperative ventral hernia epigastric, hernia, spiegelian hernia inguinal hernia, etc. is a common medical condition in which an organ protrudes through an opening in its surrounding walls (especially in the abdominal region). Hernia is sometimes treated in a tension free repair, such as implementation of meshes, patches etc. This procedure requires the insertion of a wide mesh via a relatively small aperture such that the mesh is located in a posterior layer parallel to the abdominal wall. The insertion of the mesh implants to the abdominal wall by means of laparoscopic technique or similar medical procedures requires more than one aperture and thus the abdominal wall is punctured several times. Those procedures require anesthesia and usually demand a relatively long healing time.

One of the major problems of the above procedure is the unrolling or spreading and the positioning or deploying of the mesh inside the abdominal or the pre-peritoneal cavity. The step of unrolling the mesh, directing the right side of the mesh, positioning and fixating the mesh and positioning it in the right place usually adds significantly to the time required for carrying out the procedure. Moreover, inserting the mesh/patch into the body without a trocar may expose the mesh/patch to infections.

Some techniques suggested in the literature disclose mesh-like for treating hernia. Those techniques fail to guarantee even, complete and smooth deployment of the mesh, without formation of wrinkles, and cannot ensure full anchoring of the implant to the abdominal wall.

U.S. Pat. No. 5,824,082 ('082) relates to a prosthetic hernia repair patch that can be roiled into a tube for laparoscopic delivery through a trocar and which deploys to a generally planar form when ejected from the trocar into the abdominal cavity. The deployment of the prosthetic is done by embedding a wire frame made of shape memory alloys into the prosthetic. When the prosthetic is inserted into the body it is heated thus, activated—i.e. it springs into its functional, predetermined configuration and deploys the patch. However, embedding a wire frame in a prosthetic is complicated.

Thus, there is still a long felt need for a device that is simple, will shorten the time required for the spreading and the positioning of the mesh inside the body and will be inserted via a single small-bore opening.

SUMMARY OF THE INVENTION

It is one object of the invention to disclose an inflatable contour-balloon useful in minimal invasive and/or open surgery; wherein at least a portion of said inflatable contour-balloon is positioned in the contour of a mesh and/or a patch and/or a net; further wherein said inflatable contour-balloon is adapted to spread and/or deploy said mesh and/or said patch and/or said net in the abdominal cavity and/or pre-peritoneal and/or space and/or hollow body organs and/or natural and/or artificial orifices and/or spaces and/or post operative spaces.

It is another object of the invention to disclose the inflatable contour-balloon as define above, wherein said inflatable contour-balloon is especially adapted for use in hernia repair surgery.

It is another object of the invention to disclose the inflatable contour-balloon as define above, wherein said inflatable contour-balloon additionally comprising means adapted to adjust the center of said inflatable contour-balloon to the center of said hernia.

It is another object of the invention to disclose the inflatable contour-balloon as define above, wherein said inflatable contour-balloon additionally comprising means adapted to ensure the right side of said mesh or said patch or said net is directed to said abdominal cavity and/or said pre-peritoneal and/or said space and/or said hollow body organs and/or said natural and/or said artificial orifices and/or said spaces and/or said post operative spaces.

It is another object of the invention to disclose the inflatable contour balloon as define above, wherein said inflatable contour-balloon is provided with means enabling coupling of inflating means to said inflatable contour-balloon.

It is another object of the invention to disclose the inflatable contour-balloon as define above, wherein said means is selected from a group comprising at least one radial tube, non radial tubes.

It is another object of the invention to disclose the inflatable contour-balloon as define above, wherein said inflating means is selected from a group consisting manually inflating pump, motorized inflating pump.

It is another object of the invention to disclose the inflatable contour-balloon as define above, wherein said inflatable contour-balloon is provided with means enabling threading of said mesh and/or said patch to said inflatable contour-balloon.

It is another object of the invention to disclose the inflatable contour-balloon as define above, wherein said means is selected from a group comprising at least one slit.

It is another object of the invention to disclose the inflatable contour-balloon as define above, wherein said inflatable contour-balloon is glued to said mesh and/or said patch and/or said net It is another object of the invention to disclose the inflatable contour-balloon as define above, wherein said inflatable contour-balloon is provided with means enabling sewing of said inflatable contour-balloon to said mesh and/or patch and/or said net.

It is another object of the invention to disclose the inflatable contour-balloon as define above, wherein said inflatable contour-balloon is made of a group comprising biocompatible materials, self-dissolving materials and shape memory materials.

It is another object of the invention to disclose the inflatable contour-balloon as define above, wherein the shape of said inflatable contour-balloon is selected from a group comprising a polygonal shape, a curved shape, a symmetrical, a non-symmetrical shape, a linear shape, continues, non-continues, a concave shape, a irregular shape, a square-like shape, a rectangular shape, an oval shape, a U-like shape, a grid-like shape, a flat structure, a 3D structure and a rake-like shape or any combination thereof.

It is another object of the invention to disclose the inflatable contour-balloon as define above, wherein said inflatable contour-balloon comprises at least two independent parts.

It is another object of the invention to disclose the inflatable contour-balloon as define above, wherein the configuration is as described in any of FIG. 13 to FIG. 17.

It is another object of the invention to disclose a method for spreading and/or deploying a mesh and/or a patch, useful in minimal invasive and/or open surgery. The method comprises step selected inter alia from (a) obtaining an inflatable contour-balloon as define above; (b) attaching said inflatable contour-balloon to said mesh and/or to said patch; (c) coupling said inflating means to said inflatable contour-balloon; (d) adjusting said inflatable contour-balloon; (e) inserting said adjusted inflatable contour-balloon into abdominal cavity and/or pre-peritoneal and/or hollow body organs and/or natural and/or artificial orifices and/or spaces and/or post operative spaces; and, (f) inflating at least a portion of said inflatable contour-balloon via said inflating means; thereby spreading and/or deploying said mesh and/or said patch in said abdominal cavity and/or said pre-peritoneal and/or said hollow body organs and/or said natural and/or said artificial orifices and/or said spaces and/or said post operative spaces.

It is another object of the invention to disclose the method as define above, additionally comprising the step of uncoupling said inflating means from said inflatable contour-balloon.

It is another object of the invention to disclose the method as define above, additionally comprising the step of extracting said inflatable contour-balloon from said abdominal cavity and/or said pre-peritoneal and/or said hollow body organs and/or said natural and/or said artificial orifices and/or said spaces and/or said post operative spaces.

It is another object of the invention to disclose the method as define above, additionally comprising the step of deflating said inflatable contour-balloon.

It is another object of the invention to disclose the method as define above, especially in hernia repair surgery.

It is another object of the invention to disclose the method as define above, additionally comprising the step of fitting the center of said inflatable contour-balloon to the center of said hernia.

It is another object of the invention to disclose the method as define above, additionally comprising the step of ensuring the right side of said mesh or said patch or said net is directed to said abdominal cavity and/or said pre-peritoneal and/or said space and/or said hollow body organs and/or said natural and/or said artificial orifices and/or said spaces and/or said post operative spaces.

It is another object of the invention to disclose the method as define above, additionally comprising the step of threading said mesh or/and said patch or/and said net to said inflatable contour-balloon.

It is another object of the invention to disclose the method as define above, additionally comprising the step of gluing said mesh or/and said patch or/and said net to said inflatable contour-balloon.

It is another object of the invention to disclose the method as define above, additionally comprising the step of selecting said inflatable contour-balloon from a group comprising biocompatible materials, self-dissolving materials, shape memory materials.

It is another object of the invention to disclose the method as define above, additionally comprising the step of selecting the shape of said inflatable contour-balloon from a group comprising a polygonal shape, a curved shape, a symmetrical, a non-symmetrical shape, a linear shape, continues, non-continues, a concave shape, a irregular shape, a square-like shape, a rectangular shape, an oval shape, a U-like shape, a grid-like shape, a flat structure, a 3D structure and a rake-like shape or any combination thereof.

It is another object of the invention to disclose the method as define above, additionally comprising the step of continuing inflating said inflatable contour-balloon according to a predetermined medical need.

It is another object of the invention to disclose an elongate open-bored applicator (EOBP) useful in minimal invasive surgery; said EOBP having a distal portion that is insertable into the abdominal cavity and/or pre-peritoneal and/or space and/or hollow body organs and/or natural and/or artificial orifices and/or spaces and/or post operative spaces; and a proximal portion that remains outside said body. The EOBP comprising:

a. at least one inflatable contour-balloon as defined above;
b. at least one inflatable dissection balloon; said inflatable contour-balloon and said inflatable dissection balloon are adjustable and located at said distal portion; and,
c. at least one actuating means located at said proximal portion; said actuating means is in communication with said inflatable contour-balloon and said inflatable dissection balloon; said actuating means is adapted to provide said inflatable contour-balloon and said inflatable dissection balloon with independent activation and/or de-activation;

wherein said device is adapted to spread and/or deploy a mesh and/or a patch and/or a net in said abdominal cavity and/or in said pre-peritoneal and/or in said space and/or hollow body organs and/or in said natural and/or artificial orifices and/or said spaces and/or said post operative spaces.

It is another object of the invention to disclose the EOBP as defined above, wherein said actuating means additionally comprises inflating means used to inflate said at least one inflatable dissection balloon and said at least one inflatable contour-balloon.

It is another object of the invention to disclose the EOBP as defined above, wherein said EOBP is especially adapted for use in hernia repair surgery.

It is another object of the invention to disclose the EOBP as defined above, wherein said EOBP additionally comprising means adapted to adjust the center of said inflatable contour-balloon to the center of said hernia.

It is another object of the invention to disclose the EOBP as defined above, wherein said EOBP additionally comprising means adapted to ensure the right side of said mesh or said patch or said net is directed to said abdominal cavity and/or said pre-peritoneal and/or said space and/or said hollow body organs and/or said natural and/or said artificial orifices and/or said spaces and/or said post operative spaces.

It is another object of the invention to disclose the EOBP as defined above, wherein said EOBP is provided with means enabling coupling of inflating means to said inflatable contour-balloon; and the coupling of inflating means to said inflatable dissection balloon.

It is another object of the invention to disclose the EOBP as defined above, wherein said means is selected from a group comprising at least one radial tube, non radial tubes.

It is another object of the invention to disclose the EOBP as defined above, wherein said inflating means is selected from a group comprising manually inflating pump, motorized inflating pump.

It is another object of the invention to disclose the EOBP as defined above, wherein said EOBP is provided with means enabling threading of said mesh and/or said patch to said inflatable contour-balloon.

It is another object of the invention to disclose the EOBP as defined above, wherein said means is selected from a group comprising at least one slit.

It is another object of the invention to disclose the EOBP as defined above, wherein said inflatable contour-balloon is glued to the edges of said mesh and/or said patch and/or said net.

It is another object of the invention to disclose the EOBP as defined above, wherein said EOBP is provided with means enabling sewing of said inflatable contour-balloon to said mesh and/or patch and/or said net.

It is another object of the invention to disclose the EOBP as defined above, wherein said inflatable contour-balloon and/or said dissection balloon is made of a group comprising biocompatible materials, self-dissolving materials and shape memory materials.

It is another object of the invention to disclose the EOBP as defined above, wherein the shape of said inflatable contour-balloon and/or said inflatable dissection balloon is selected from a group comprising a polygonal shape, a curved shape, a symmetrical, a non-symmetrical shape, a linear shape, continues, non-continues, a concave shape, a irregular shape, a square-like shape, a rectangular shape, an oval shape, a U-like shape, a grid-like shape, a flat structure, a 3D structure and a rake-like shape or any combination thereof.

It is another object of the invention to disclose the EOBP as defined above, wherein said inflatable contour-balloon comprises at least two independent parts.

It is another object of the invention to disclose the EOBP as defined above, configured as described in any of FIG. 13 to FIG. 17.

It is another object of the invention to disclose the EOBP as defined above, configured as described in any of FIG. 10*a* to FIG. 10*g*.

It is another object of the invention to disclose a method for spreading and/or deploying a mesh and/or a patch, useful in minimal invasive and/or open surgery. The step comprises step selected inter alia from (a) obtaining an EOBP as defined above; (b) attaching said inflatable contour-balloon to said mesh and/or to said patch; (c) coupling said inflating means to said inflatable contour-balloon and said inflatable dissection balloon; (d) adjusting said inflatable contour-balloon and said inflatable dissection balloon; (e) introducing said device into abdominal cavity and/or pre-peritoneal and/or hollow body organs and/or natural and/or artificial orifices and/or spaces and/or post operative spaces; and, (f) inflating at least a portion of said inflatable contour-balloon via said inflating means; thereby spreading and/or deploying said mesh and/or said patch in said abdominal cavity and/or said pre-peritoneal and/or said hollow body organs and/or said natural and/or said artificial orifices and/or said spaces and/or said post operative spaces.

It is another object of the invention to disclose the method as defined above, additionally comprising the step of inflating at least a portion of said inflatable dissection balloon via said inflating means.

It is another object of the invention to disclose the method as defined above, additionally comprising the step of uncoupling said inflating means from said inflatable contour-balloon.

It is another object of the invention to disclose the method as defined above, additionally comprising the step of uncoupling said inflating means from said inflatable dissection balloon.

It is another object of the invention to disclose the method as defined above, additionally comprising the step of deflating said inflatable contour-balloon.

It is another object of the invention to disclose the method as defined above, additionally comprising the step of deflating said inflatable dissection balloon.

It is another object of the invention to disclose the method as defined above, additionally comprising the step of extracting said inflatable contour-balloon from said abdominal cavity and/or said pre-peritoneal and/or said hollow body organs and/or said natural and/or said artificial orifices and/or said spaces and/or said post operative spaces.

It is another object of the invention to disclose the method as defined above, additionally comprising the step of extracting said inflatable dissection balloon from said abdominal cavity and/or said pre-peritoneal and/or said hollow body organs and/or said natural and/or said artificial orifices and/or said spaces and/or said post operative spaces.

It is another object of the invention to disclose the method as defined above, especially in hernia repair surgery.

It is another object of the invention to disclose the method as defined above, additionally comprising the step of fitting the center of said inflatable contour-balloon to the center of said hernia.

It is another object of the invention to disclose the method as defined above, additionally comprising the step of ensuring the right side of said mesh or said patch or said net is directed to said abdominal cavity and/or said pre-peritoneal and/or said space and/or said hollow body organs and/or said natural and/or said artificial orifices and/or said spaces and/or said post operative spaces.

It is another object of the invention to disclose the method as defined above, additionally comprising the step of threading said mesh or/and said patch or/and said net to said inflatable contour-balloon.

It is another object of the invention to disclose the method as defined above, additionally comprising the step of gluing said mesh or/and said patch or/and said net to said inflatable contour-balloon.

It is another object of the invention to disclose the method as defined above, additionally comprising the step of selecting said inflatable contour-balloon and/or said inflatable dissection balloon from a group comprising biocompatible materials, self-dissolving materials, shape memory materials.

It is another object of the invention to disclose the method as defined above, additionally comprising the step of selecting the shape of said inflatable contour-balloon and/or said inflatable dissection balloon from a group comprising a polygonal shape, a curved shape, a symmetrical, a non-symmetrical shape, a linear shape, continues, non-continues, a concave shape, a irregular shape, a square-like shape, a rectangular shape, an oval shape, a U-like shape, a grid-like shape, a flat structure, a 3D structure and a rake-like shape or any combination thereof.

It is another object of the invention to disclose the EOBP as defined above, wherein said actuating means are adapted to extract said inflatable contour-balloon and/or said inflatable dissection balloon from said abdominal cavity and/or in said pre-peritoneal and/or in said space and/or hollow body organs and/or in said natural and/or artificial orifices and/or said spaces and/or said post operative spaces.

It is another object of the invention to disclose the EOBP as defined above, additionally comprising means adapted to anchor said EOBP in said abdominal cavity and/or in said pre-peritoneal and/or in said space and/or hollow body organs and/or in said natural and/or artificial orifices and/or said spaces and/or said post operative spaces.

It is still an object of the invention to disclose the method as defined above, additionally comprising the step of continuing inflating said inflatable dissection balloon according to a predetermined medical need.

It is lastly an object of the invention to disclose the method as defined above, additionally comprising the step of continuing inflating said inflatable contour-balloon according to a predetermined medical need.

BRIEF DESCRIPTION OF THE FIGURES

In order to understand the invention and to see how it may be implemented in practice, a plurality of preferred embodiments will now be described, by way of non-limiting example only, with reference to the accompanying drawings, in which FIG. 1 schematically present general view of the of the elongate open-bored applicator.

FIGS. 7a to 7e schematically present the mesh implanting process according to one embodiment of the present invention.

FIGS. 9a to 9g present possible solutions or means for centering the mesh with respect to the inflatable dissection balloon.

FIGS. 11a-11d present possible valve designs for sealing the airway of the inflatable contour-balloon.

FIGS. 20a and 20b display a more detail look of the same.

FIGS. 20c-20e display a different way to couple the inflatable contour-balloon and the mesh.

DETAIL DESCRIPTION OF THE INVENTION

Figure 1:
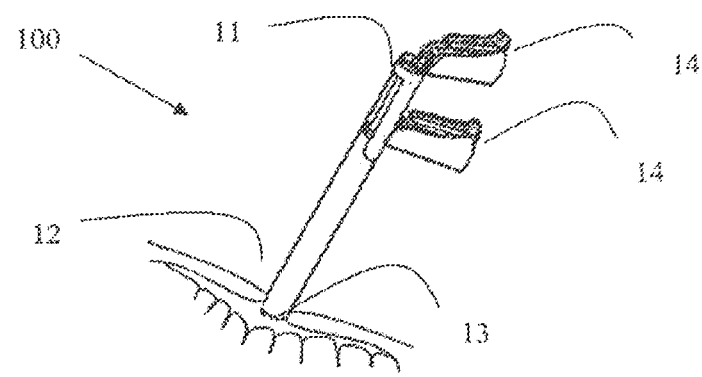
FIGS. 1a-1d schematically display wings-like means adapted to anchor the elongate open-bored applicator 100 within the tissue and to thrust the tissue.

The following description is provided, alongside all chapters of the present invention, so as to enable any person skilled in the art to make use of said invention and sets forth the best modes contemplated by the inventor of the carrying out this invention. Various modifications, however, is adapted to remain apparent to those skilled in the art, since the generic principles of the present invention have been defined specifically to provide an inflatable contour-balloon useful in minimal invasive and/or open surgery. The inflatable contour-balloon positioned in the contour of a mesh and/or a patch and/or a net. The inflatable contour-balloon is adapted to spread and/or deploy a mesh and/or a patch and/or a net in the abdominal cavity and/or pre-peritoneal and/or space and/or hollow body organs and/or natural and/or artificial orifices and/or spaces and/or post operative spaces.

The present invention also provides a method for spreading and/or deploying a mesh and/or a patch, useful in minimal invasive and/or open surgery. The method comprises step selected inter alia from (a) obtaining an inflatable contour-balloon; (b) attaching the inflatable contour-balloon to the mesh and/or to the patch; (c) coupling the inflating means to the inflatable contour-balloon; (d) adjusting the inflatable contour-balloon; (e) inserting the adjusted inflatable contour-balloon into abdominal cavity and/or pre-peritoneal and/or hollow body organs and/or natural and/or artificial orifices and/or spaces and/or post operative spaces; and (f) inflating at least a portion of the inflatable contour-balloon via the inflating pump; thereby spreading and/or deploying said mesh and/or the patch in the abdominal cavity and/or the pre-peritoneal and/or the hollow body organs and/or the natural and/or the artificial orifices and/or the spaces and/or the post operative spaces.

The present invention also provides a device adapted to spread and/or deploy a mesh and/or a patch, useful in minimal invasive and/or open surgery. The device comprising: (a) at least one inflatable contour-balloon; (b) one inflatable dissection balloon; (c) at least one actuating means. The device is adapted to spread and/or deploy a mesh and/or a patch and/or a net in the abdominal cavity and/or pre-peritoneal and/or space and/or hollow body organs and/or natural and/or artificial orifices and/or spaces and/or post operative spaces.

The present invention also provides a method for spreading and/or deploying a mesh and/or a patch, useful in minimal invasive and/or open surgery. The method comprises step selected inter alia from (a) obtaining a device; (b) attaching the inflatable contour-balloon to the mesh and/or to the patch; (c) coupling the inflating means to the inflatable contour-balloon and the inflatable dissection balloon; (d) adjusting the inflatable contour-balloon and the inflatable dissection balloon; (e) introducing the device into abdominal cavity and/or pre-peritoneal and/or hollow body organs and/or natural and/or artificial orifices and/or spaces and/or post operative spaces; (f) inflating at least a portion of the inflatable dissection balloon via the inflating means; and, (g) at least a portion of inflating the inflatable contour-balloon via the inflating means; thereby spreading and/or deploying the mesh and/or the patch in the abdominal cavity and/or the pre-peritoneal and/or the hollow body organs and/or the natural and/or the artificial orifices and/or the spaces and/or the post operative spaces.

The methods can comprise steps selected inter alia from extracting the inflatable contour-balloon and/or the inflatable dissection balloon from the abdominal cavity and/or the pre peritoneal and/or the hollow body organs and/or the natural and/or the artificial orifices and/or the spaces and/or the post operative spaces; continuing inflating the inflatable contour-balloon and/or the inflatable dissection balloon according to a predetermined medical need; deflating the inflatable contour-balloon and/or the inflatable dissection balloon.

The term "balloon" refers hereinafter to any flexible bag which can inflates or expands. The balloon can be made from materials such as rubber, latex, silicone, polyurethane, chloroprene or a nylon fabric or any thermoelastomeric materials. The balloon can be made of biocompatible materials, self-dissolving materials or shape memory materials.

The term "Hernia" refers hereinafter for umbilical hernia, hiatal hernia, ventral hernia, postoperative hernia, epigastric hernia, spiegelian hernia, inguinal hernia and femoral hernia, generally any abdominal wan related hernia.

The term "minimally invasive surgery" refers hereinafter to a procedure that is carried out by entering the body through the skin or through a body cavity or anatomical opening, but with the smallest damage possible.

The term "Biocompatible materials" refers hereinafter to materials that have the ability to perform with an appropriate host response in a specific application. Biocompatible materials have the quality of not having toxic or injurious effects on biological systems.

The term "self-dissolving materials" refers hereinafter to materials that are degraded by the body's enzymatic and/or hydrolytic pathways through a reaction against "foreign" material. Some urologists may prefer self-dissolving materials in catheter simply because then they don't have to go necessarily through the procedure of removing them afterwards. Examples of self-dissolving polymers are Polydioxanone (PDO), Polycaprolactone (PCL), Polylactic acid (PLA), Polyglycolic acid (PGA), Adipic acid, PEG and glutamic acid.

The term "shape memory materials" refers hereinafter to materials which can "remember" there original geometry. After a sample of shape memory materials has been deformed from its original geometry, it regains its original geometry by itself during heating (one-way effect) or, at higher ambient temperatures, simply during unloading (pseudo-elasticity or superelasticity). The thermally induced shape-memory effect has been described for different material classes: polymers, such as polyurethanes, poly(styrene-block-butadiene), Polydioxanone and polynorbornene, metallic alloys, such as copper-zine-aluminium-nickel, copper-aluminium-nickel, and nickel-titanium (NiTi) alloys.

The term "adjusting" or "adjustable" refers hereinafter to rolling, bending, twisting, folding and winding.

The term "activation" refers hereinafter to the act of inflating a balloon.

The term "de-activation" refers hereinafter to the act of deflating the balloon (i.e. extracting the air out of the balloon).

The term "contour" refers hereinafter to any section (and not only to the outer edge) of the mesh and/or patch and/or net.

Figure 2:
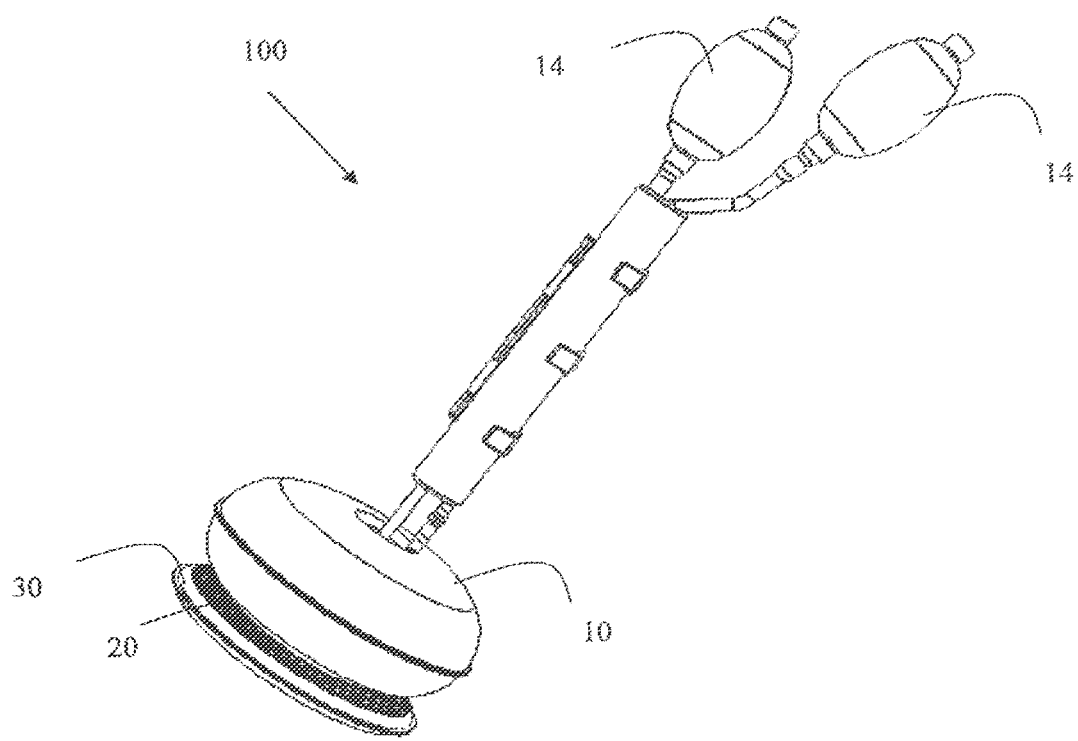
FIG. 2 schematically display the elongate open-bored applicator once the posterior portion is inside the body.
Figure 2A:
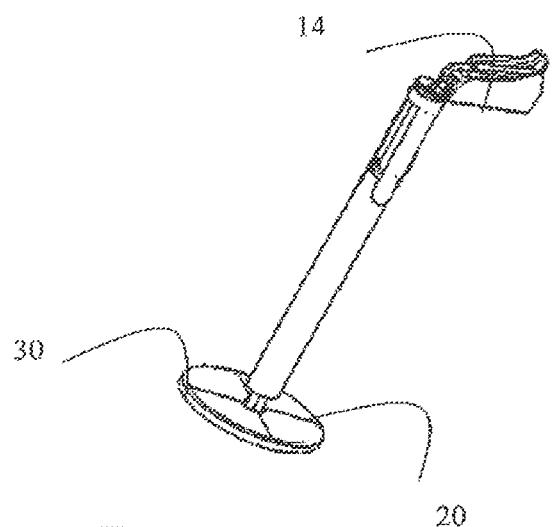
FIGS. 2a-2d schematically present general view of the applicator, the inflatable dissection balloon, the inflatable contour-balloon and the mesh.
Figure 2B:
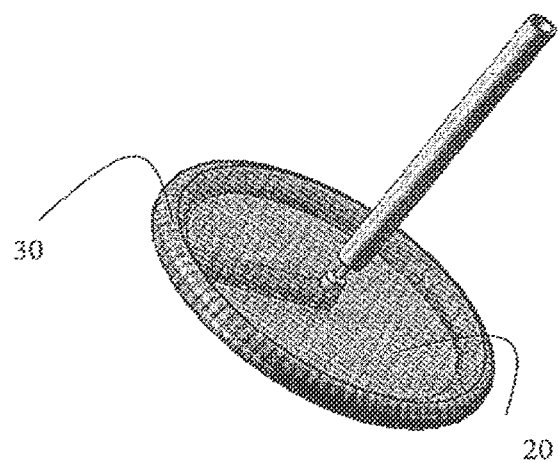
Figure 2C:
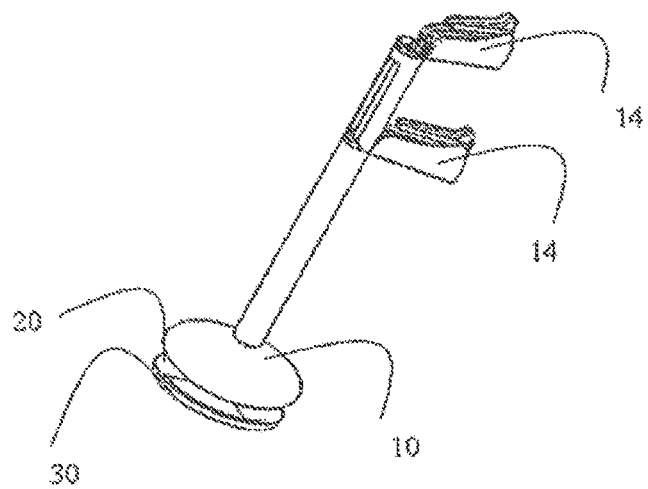
Figure 2D:
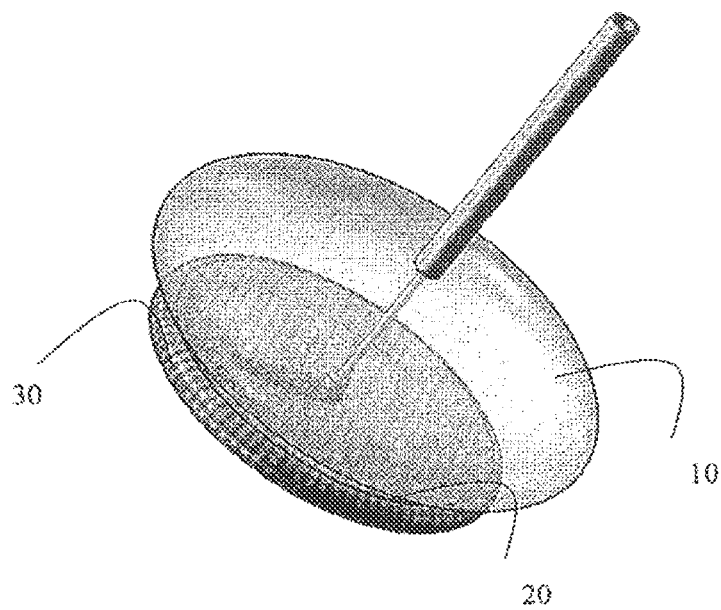

Reference is now FIGS. 1-2d, which schematically present a general view of the elongate open-bored applicator 100 according to the present invention. The elongate open-bored applicator 100 has an anterior portion 11 terminated outside the body and a posterior portion 12 terminated with an orifice 13 insertable into the abdominal cavity abdominal cavity and/or pre-peritoneal and/or space and/or hollow body organs and/or natural and/or artificial orifices and/or spaces and/or post operative spaces. The elongate open-bored applicator 100 comprises at least one inflatable contour-balloon 30, which is attached to the contours of mesh 20 (the different ways of attaching the inflatable contour balloon 30 to mesh 20 will be discussed later on in the detail description). The elongate open-bored applicator 100 may additionally comprises a second inflatable balloon (refers herein after as inflatable dissection balloon) 10. The mesh and the inflatable contour-balloon are adjusted to lit inside the applicator 100. Mesh 20 is adapted to deploy when injected outside the applicator inside the body cavity. The elongate open-bored applicator 100 additionally comprises actuating means 14 adapted to push mesh 20 throughout the applicator via said posterior orifice 13. The actuating means 14 can comprises a maneuverable pistol and/or handles operating the same (denotes as 14 in FIG. 1) or inflating pumps for inflating the inflatable dissection balloon 10 and the inflatable contour-balloon 30 (denotes as 14 in FIG. 2).

Figures 1A, 1B:
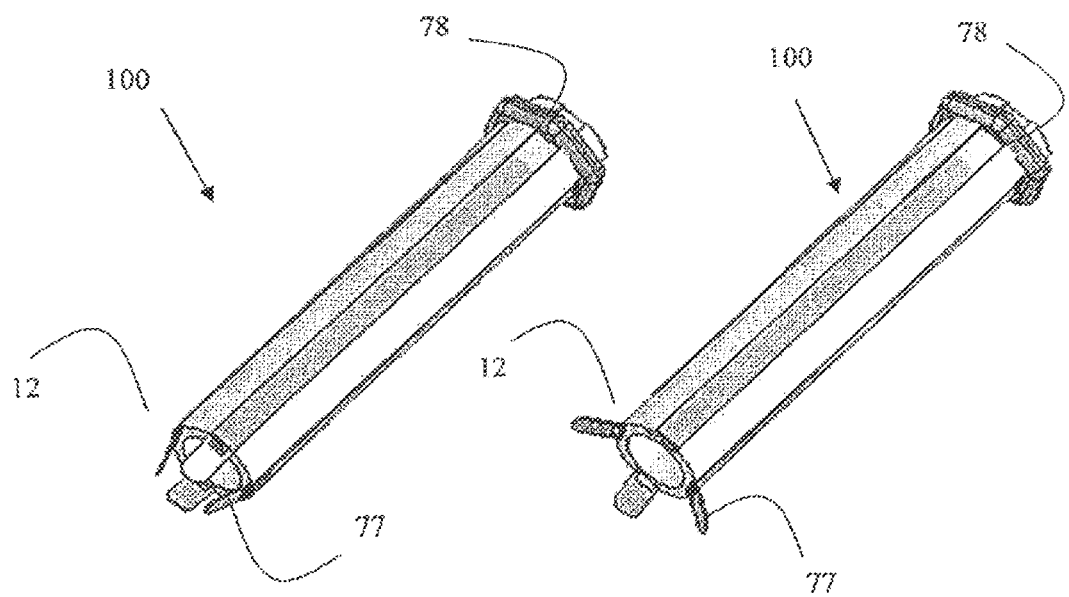

Reference is now made to FIGS. 1a-1b, which schematically display wings-like means 77 adapted to anchor the elongate open-bored applicator 100 within the tissue and to thrust the tissue. The wings-like means 77 are positioned in the posterior portion 12. FIG. 1a represent the wings-like means 77 in a semi open configuration and FIG. 1b represents the wings-like means 77 in a fully open configuration. Activation means 78 are also provided for activating (i.e. opening and closing) the wings-like means 77. The activation or de-activation of the wings-like means 77 by the activation means 78 can be performed by sliding the activation means 78 towards and away from the posterior portion 12.

Figure 1C:
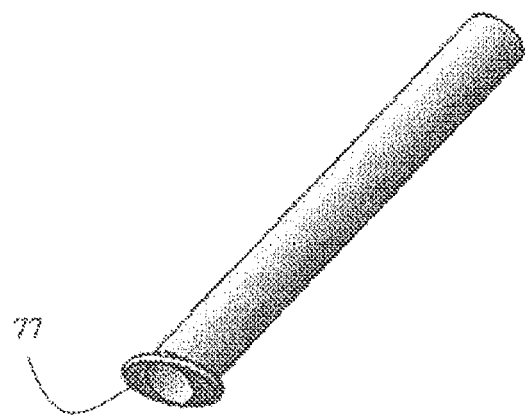
Figure 1D:
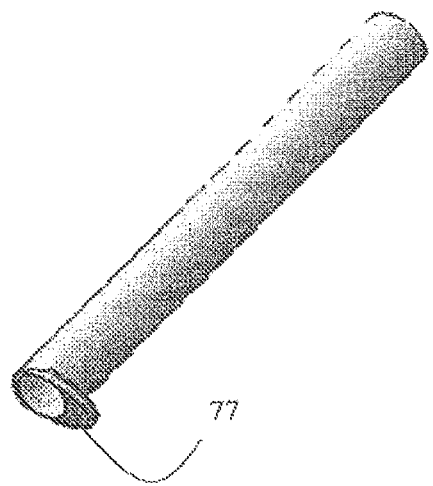

The wings-like means 77 can have the configuration as shown in FIGS. 1c-1d. In those figures the wings-like means 77 are fixed in their positions.

Reference is now made to FIG. 2 which schematically display the elongate open-bored applicator 100 once the posterior portion 12 is inside the body. As can be seen from FIG. 2, both the inflatable dissection balloon 10 and the inflatable contour-balloon 30 are inflated so as mesh 20 is in parallel to the wall of the abdominal cavity.

The modus in which both the balloon are inflated can include different timing. For example, the inflatable contour-balloon 30 is inflated to about 50% of its volume, then the inflatable dissection balloon 10 is inflated to about 70% of its volume, and then the inflation of the inflatable contour-balloon 30 is completed.

The actuating means 14 are represented in FIG. 2 as two pumps 14 used for inflating balloons 10 and 30. It should be pointed out that the present invention is not limited to the use of two pumps. One pump can be used to inflate both balloons 10 and 20 (as seen in FIG. 2a).

Reference is now made to FIGS. 2a and 2b schematically present general view of the applicator, the inflatable contour-balloon 30 and mesh 20. According to FIG. 2a the applicator 100 comprises only the inflatable contour-balloon 30. FIG. 2b is an enclose view of the inflatable contour-balloon 30 and mesh 20.

Reference is now made to FIGS. 2c and 2d schematically present general view of the applicator, the inflatable dissection balloon 10, the inflatable contour-balloon 30 and mesh 20. As can be seen in FIG. 2c, the applicator 100 comprises the inflatable contour-balloon 30 and inflatable dissection balloon 10. FIG. 2d is an enclose view of the inflatable contour-balloon 30, the inflatable dissection balloon 10 and mesh 20.

Those figures (FIGS. 2a-2d) also display the actuating means 14 (which are handles is in those figures) enabling the surgeon to control and to pump air into the inflatable contour-balloon 30 and to the inflatable dissection balloon 10.

The elongate open-bored applicator is activated as follows: applicator 100 is introduced into the wall of the abdominal cavity. Next, at least a portion of the inflatable dissection balloon 10 is inflated, hence thrusting. Then the inflatable contour-balloon 30 which is attached to mesh 30 is inflated to a predetermined size, such that said mesh is laying in parallel to said wall. Next, the inflatable dissection balloon 10 is deflated and evacuated throughout said applicator 100. Finally, applicator 100 is removed and mesh 20 is fastened to the posterior abdominal wall.

Contour-balloon 30 and/or the inflatable dissection balloon 10 can be made of a group comprising biocompatible materials, self-dissolving materials such that after a period of time only mesh 20 stays connected to the tissue. Inflatable contour-balloon 30 can be made of shape memory materials.

Inflatable contour-balloon 30 may be covered with mesh 20 all-around. Furthermore, inflatable contour-balloon 30 can be removed out of the body when mesh 20 is fully spread.

The shape of the inflatable contour-balloon 30 and/or the inflatable dissection balloon 10 can be a polygonal shape, a curved shape, a symmetrical, a non-symmetrical shape, a linear shape, continues, non-continues, a concave shape, a irregular shape, a square-like shape, a U-like shape, a grid-like shape and a rake-like shape or any combination thereof.

Mesh 20 is attached to the inflatable contour-balloon 30 by means of gluing, sewing, or threading the mesh into the inflatable contour-balloon 30. Another option to couple the mesh to the balloon is by velcro. The mesh can be attached to the inflatable contour-balloon 30 by means of gluing the balloon to the mesh such that the balloon remains in the body. Another option is to glue the mesh to the inflatable contour-balloon 30 such that the balloon can be separated from the mesh and extracted from the body. I.e., only the mesh remains in the body. The actuating means 14 can be used for extracting the inflatable contour-balloon 30 and/or the inflatable dissection balloon 10.

Another option is to use the mesh as bedding for building the inflatable contour-balloon 30. A proofing material is spread on the mesh's fibers. The inflatable contour-balloon 30 will be created by folding the edges of mesh.

Both the balloons (30 or 10) can be inflated by air, $CO_2$, saline etc.

Figure 3:
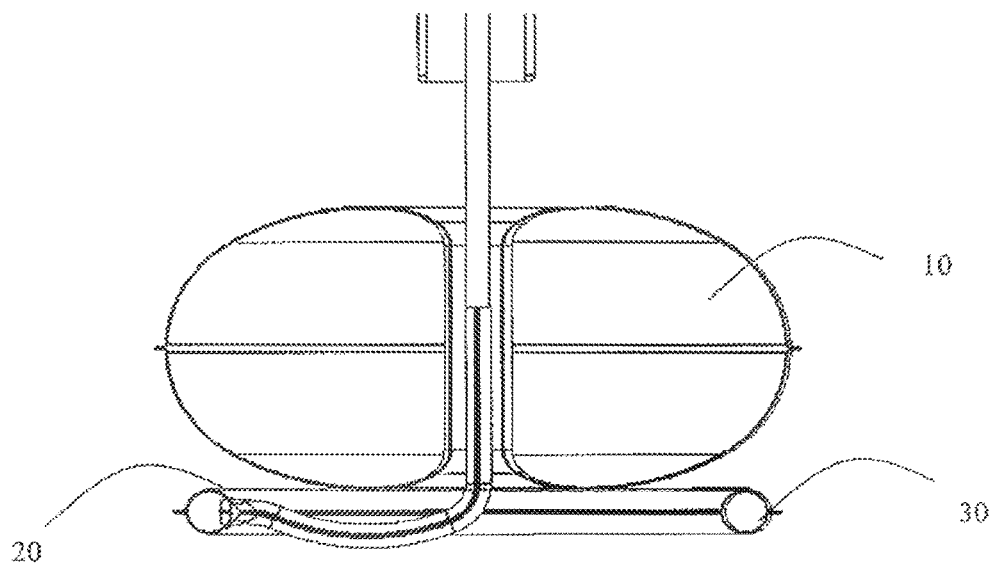
FIG. 3 schematically presents cut view of the in the middle of the applicator.

Reference is now made to FIG. 3, which schematically presents cut view of the middle of the applicator 100 showing mesh 20, inflatable contour-balloon 30, inflatable dissection balloon 10 and the relation between them.

Figures 4A, 4B:
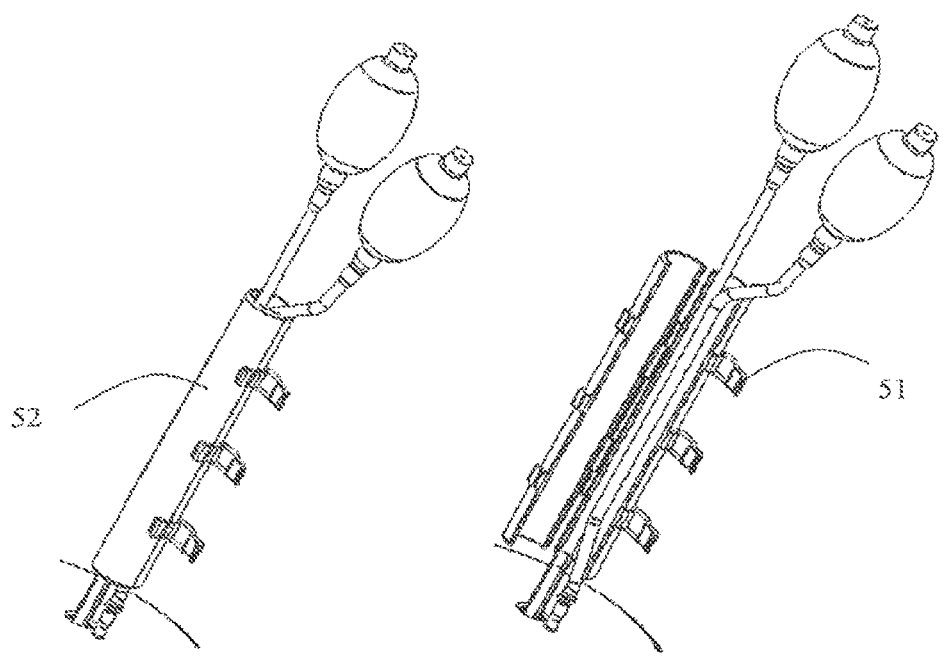
FIG. 4a and FIG. 4b displaying an applicator according to another embodiment of the present invention.

Reference is now made to FIG. 4a and FIG. 4b displaying an applicator according to another embodiment of the present invention. According to this embodiment, the applicator additionally comprising a cover 52 and means 51 enabling the surgeon to pull aside the cover 52 from the balloons system.

Figure 5:
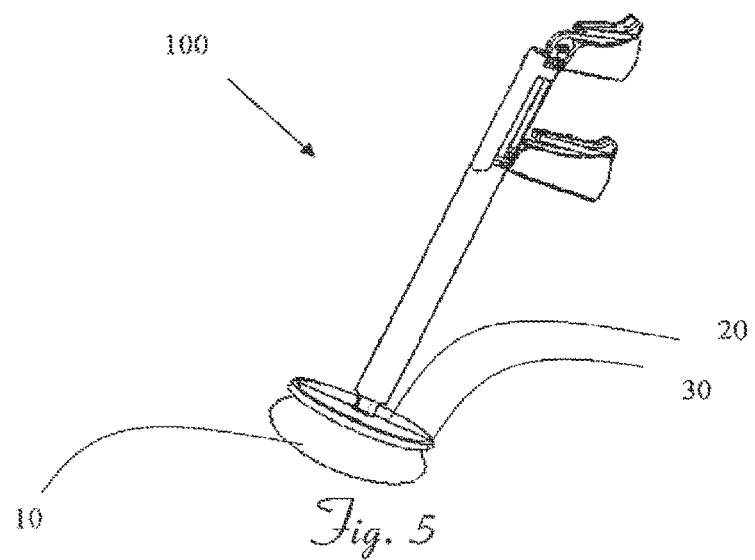
FIG. 5 schematically presents the applicator according to another embodiment of present invention.

Reference is now made to FIG. 5, displays the applicator according to another embodiment of the present invention. According to this embodiment, the inflatable contour-balloon 30 is positioned above the inflatable dissection balloon 10.

Figure 6A:
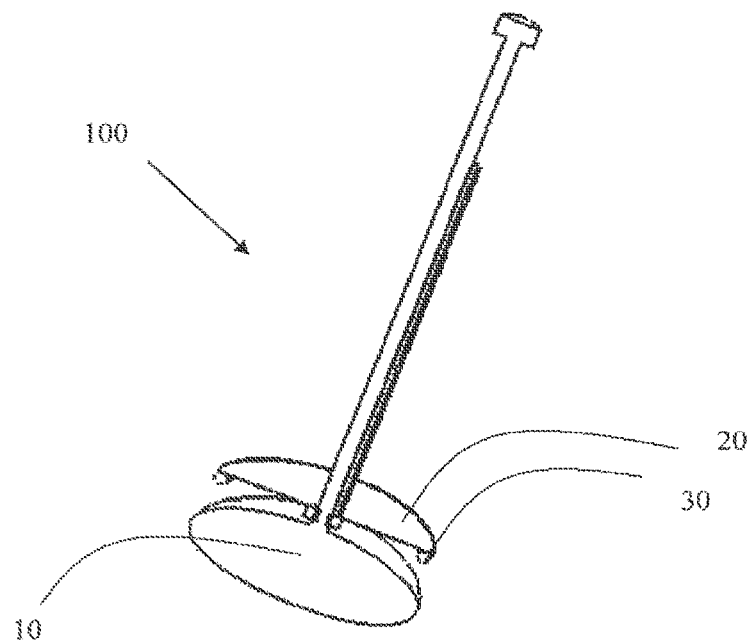
FIG. 6a, presents a cut view in the middle of the applicator 100 according to the embodiment described in FIG. 5.

FIG. 6a schematically presents a cut view in the middle of the applicator 100 according to the embodiment described in FIG. 5.

Figure 6B:
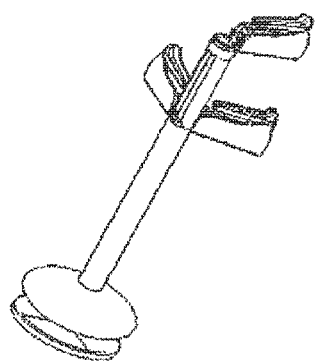
FIG. 6b displays the applicator according to another embodiment of the present invention.

FIG. 6b displays the applicator according to another embodiment of the present invention. According to this embodiment, the inflatable contour-balloon 30 comprises two independent parts (as seen clearly from FIG. 20i or 20j which display a balloon comprising several independent parts). Furthermore, the applicator according to this embodiment comprises three handles: one for the inflatable dissection balloon 10 and two for the inflatable contour-balloon (one for each part).

Reference is now made to FIGS. 7a to 7e, which schematically present the mesh implanting process according to one embodiment of the present invention. According to this embodiment, the mesh is spread by using the inflatable contour-balloon 30 only (without the inflatable dissection balloon 10).

According to this embodiment, the applicator 100 comprises mesh 20 and the inflatable contour-balloon 30.

FIG. 7a schematically shows the surgeon check the hernia area through the incision made by the surgeon.

FIG. 7b schematically displays the placement of applicator 100 in the incision made by the surgeon.

In FIG. 7c the inflatable contour-balloon 30 is inflated (thus producing a cavity in which the mesh will be placed) and mesh 20 is spread in its anterior part.

FIG. 7d shows the surgeon insuring, through the incision, that mesh 20 is fully spread.

FIG. 7e shows the incision closed with stitches.

Reference is now made to FIGS. 8a to 8e, which schematically present the mesh implanting process according to another embodiment of the present invention:

According to this embodiment, the applicator 100 comprises mesh 20, the inflatable contour-balloon 30 and the inflatable dissection balloon 10.

Figures 8A, 8B:
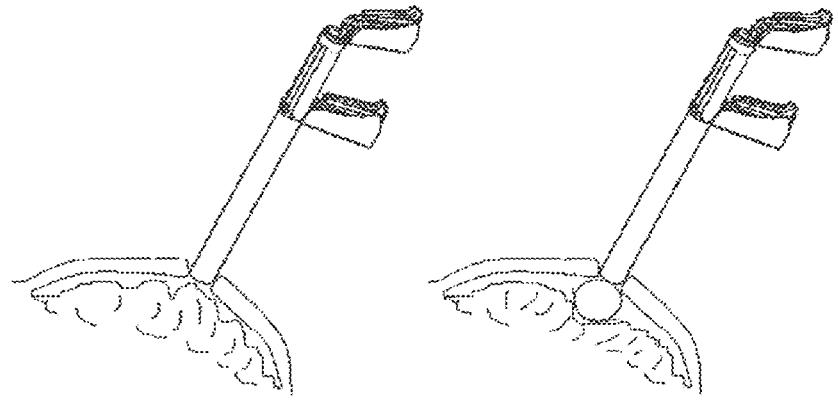
FIGS. 8a to 8e schematically present the mesh implanting process according to another embodiment of the present invention.

FIG. 8a represents the first step in which the applicator 100 is placed in the incision made by the surgeon.

FIG. 8b represents the second step in which the inflatable dissection balloon 10 is semi inflated starting to produce a cavity in which mesh 20 will be spread in.

Figures 8C, 8D:
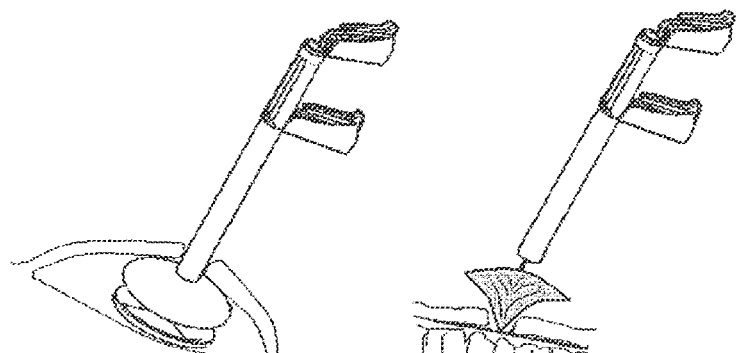

FIG. 8c represents the next step in which the inflatable dissection balloon 10 is inflated and the inflatable contour-balloon 30 is inflated thus mesh 20 is spread in its anterior part.

FIG. 8d represents the next step in which the inflatable dissection balloon 10 is emptied and drawn out from the incision while mesh 20 stays spread around the incision and lying in parallel to abdominal wall.

Figure 8E:
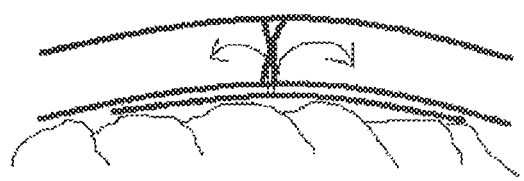

FIG. 8e represents the last step in which the incision is closed with stitches.

Figure 9A:
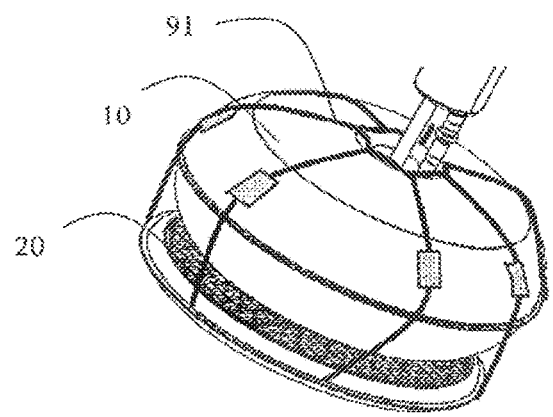
Figure 9B:
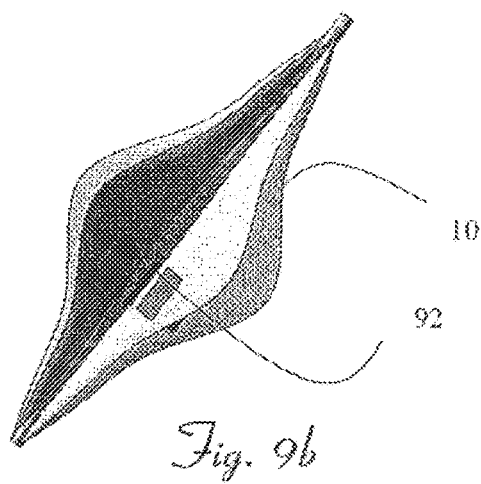
Figure 9C:
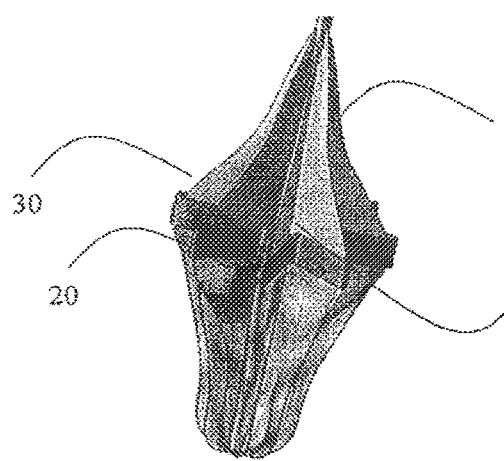

Reference is now made to FIGS. 9a, 9b and 9c presenting a possible solutions or means for centering mesh 20 with respect to the inflatable dissection balloon 10.

In FIG. 9a, centralization of mesh 20 may be realized with wires 91 stretching from the posterior side of the inflatable dissection balloon 10 to mesh 20.

Figure 9D:
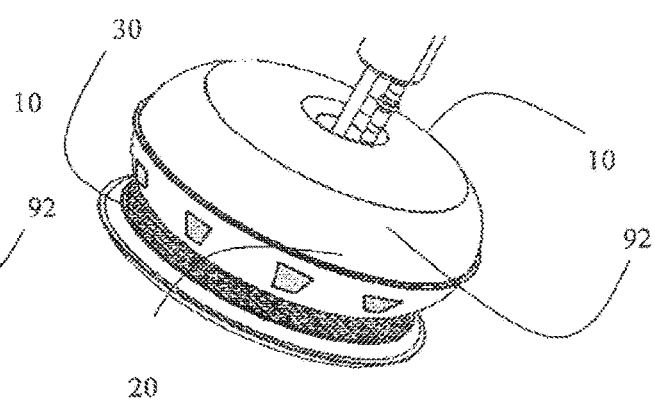

Centralization of mesh 20 is realized by using Velcro and/or double sided masking tape and/or small Silicon tubes 92 that hold the mesh until the inflatable dissection balloon 10 is inflated enough to tear the connection. FIG. 9b displays the inflatable dissection balloon 10 with Velcro and/or double sided masking tape and/or small Silicon tubes 92. FIG. 9c displays the inflatable dissection balloon 10 with Velcro and/or double sided masking tape and/or small Silicon tubes 92, attached/combined/adjusted with the inflatable contour-balloon 30 and mesh 20. FIG. 9d displays the Velcro and/or double sided masking tape and/or small Silicon tubes 92 after the inflatable dissection balloon 10 is inflated enough such that the connection between the inflatable dissection balloon 10 and mesh 20 is torn apart.

In FIGS. 9e-9f centralization of mesh 20 is made by a ribbon 90 that surrounds the balloon and holds the mesh tight to the dissection balloon. When the inflatable dissection balloon 10 is inflated, the ribbon expands until mesh 20 is relapsed. FIG. 9e displays the inflatable dissection balloon 10 is inflated such that mesh 20 is relapsed. FIG. 9f displays the inflatable dissection balloon 10 prior to the inflation.

In FIG. 9g, rigid but flexible stripes 91 are leaning on the inflatable contour-balloon 30 just like the mechanism of an umbrella, when the stripes 91 are pushed they stretch mesh 20. The inflatable dissection balloon 10 makes room in between the tissues and strengths the central part of the mesh 20.

Reference is now made to FIGS. 10a-10g presenting possible designs of the inflatable dissection balloon 10 and possible coupling options between said inflatable balloon 10 and the mesh 20. As can be seen from the figures tube 101 is used to inflate the inflatable dissection balloon 10 and tube 102 is used to inflate the inflatable contour-balloon 30.

Figure 10A:
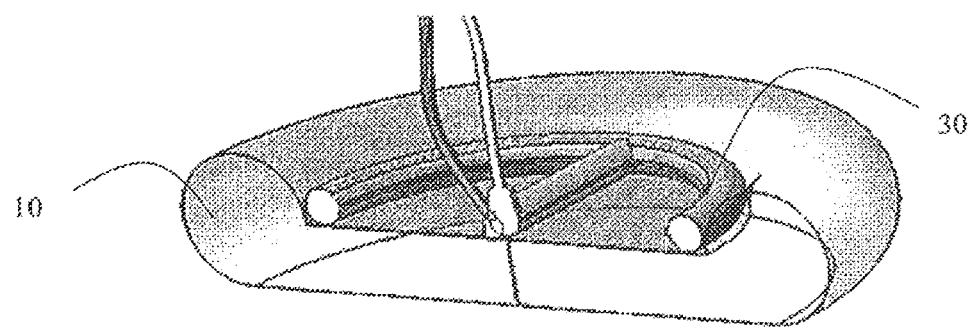
FIGS. 10a-10g present possible designs of the inflatable dissection balloon and possible coupling options between said inflatable balloon and the mesh.
Figure 10B:
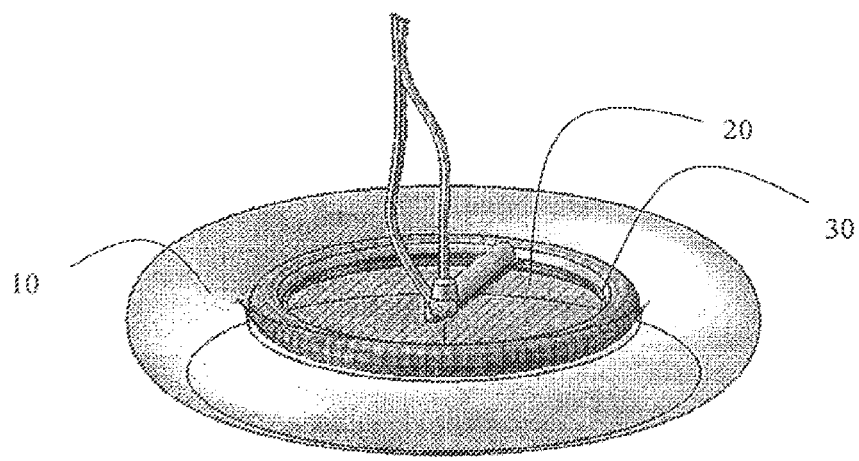

As can be seen from FIGS. 10a and 10b the inflatable dissection balloon 10 surrounds mesh 20 and the inflatable contour-balloon 30.

In FIGS. 10a-10b mesh 20 and the inflatable contour-balloon 30 are positioned in the internal portion of the inflatable dissection balloon 10. FIG. 10a is a cut view of the same.

Figure 10C:
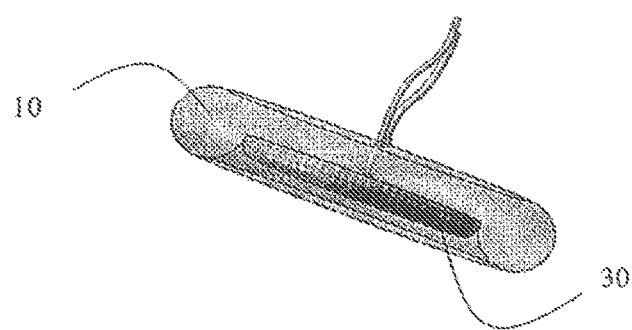
Figure 10D:
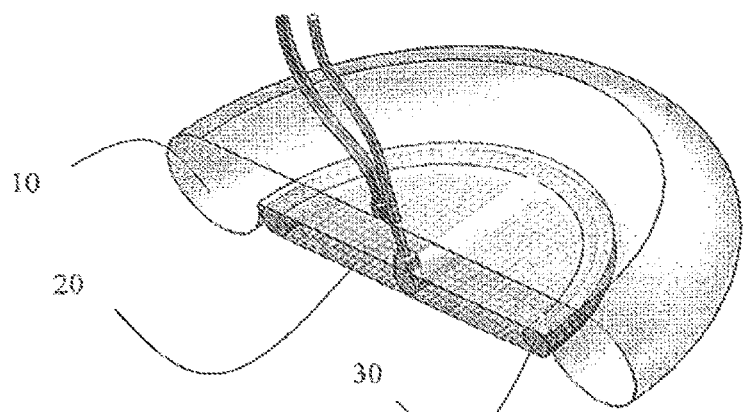
Figure 10E:
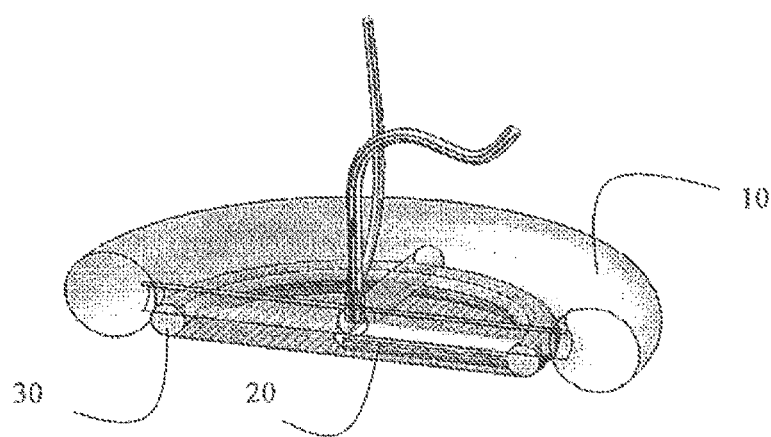

In FIG. 10c mesh 20 and the inflatable contour-balloon 30 are positioned in the internal portion of the inflatable dissection balloon 10. FIG. 10d is a cut view of the same. The difference between FIGS. 10a and 10e is the location of the two balloon with respect to each other. In FIGS. 10a and 10b the inflatable dissection balloon 10 surrounds mesh 20 and the inflatable contour-balloon 30 from bellow and in FIGS. 10c and 10d the inflatable dissection balloon 10 surrounds mesh 20 and the inflatable contour-balloon 30 from above.

In FIG. 10e mesh 20 and the inflatable contour-balloon 30 are positioned in the inner portion 103 of the inflatable dissection balloon 10.

Figure 10F:
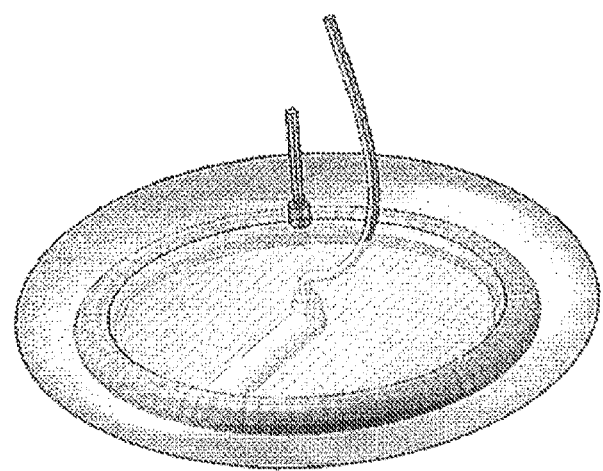
Figure 10G:
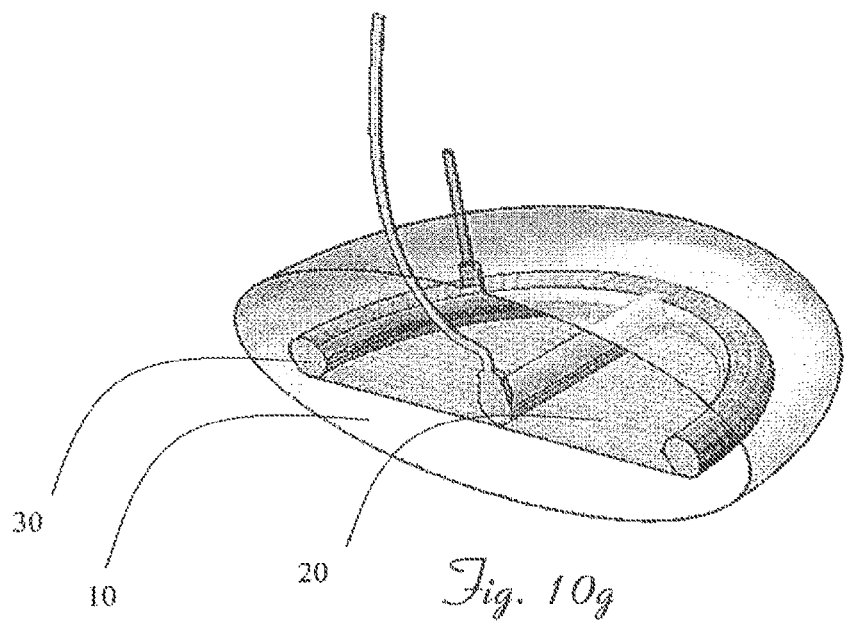

In FIG. 10f mesh 20 and the inflatable contour-balloon 30 are incorporated within inflatable dissection balloon 10. FIG. 10g is a cut view of the same.

Reference is now made to FIGS. 11a-11d presenting possible valve designs for sealing the airway of the inflatable contour-balloon 30:

FIG. 11a displays a possible valve design according to one embodiment of the present invention. According to this embodiment, a rigid tube 110 in inserted into the flexible inflating tube 102. The inside portion of the tube 102 is covered with glue 111. When the rigid tube 110 is drawn out of the flexible inflating tube 102, the inside portion of said tube 102 stick together and do not allow air to escape.

FIG. 11b displays another possible design of a valve. In this embodiment, the valve is made of a rigid tube 113. The rigid tube 113 is positioned inside the flexible inflating tube 102. In the inside of the flexible inflating tube 102 there are leafs 114 covered with glue. When the rigid tube 113 is drawn out of the flexible inflating tube 102, leafs 114 inside the inflating tube 102 expand and stick to each other and thus do not allow air to escape.

FIGS. 11c and 11d display a rubber band 115 positioned around the rigid tube 116. When the rigid tube 116 is drawn out of the flexible inflating tube 102 (see FIG. 11d), the rubber band 116 applies force on the flexible inflating tube 102 and thus do not allow air to escape.

Figure 12:
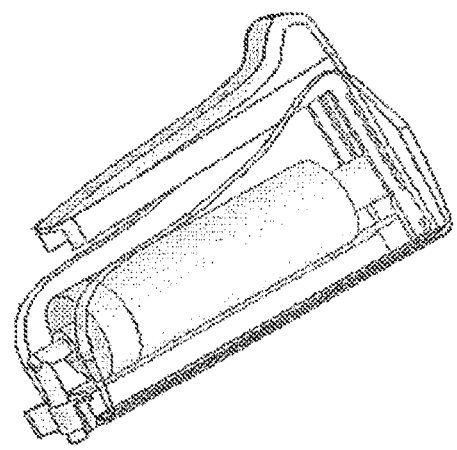
FIG. 12 presents a possible design a handle which is also used as an air pump.

Reference is now made to FIG. 12, which presents a possible design a handle which is also used as an air pump. The air pump can be used either to pump air or to empty the air out of the inflatable contour-balloon 30.

Reference is now made to FIG. 13, which schematically displays different designs of the inflatable contour-balloon 30.

Figures 13A, 13B, 13C:
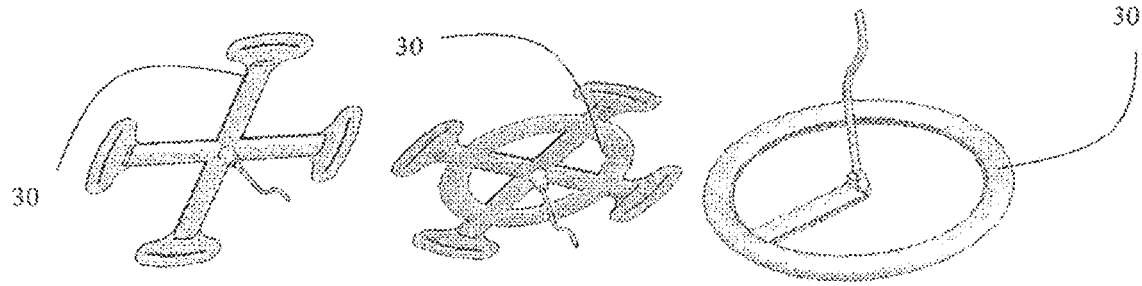
FIGS. 13a-13o schematically display a different design of the inflatable contour-balloon; furthermore FIGS. 13a-13o display different options for connecting the mesh/net/patch to the balloons.
Figures 13D, 13E, 13F:
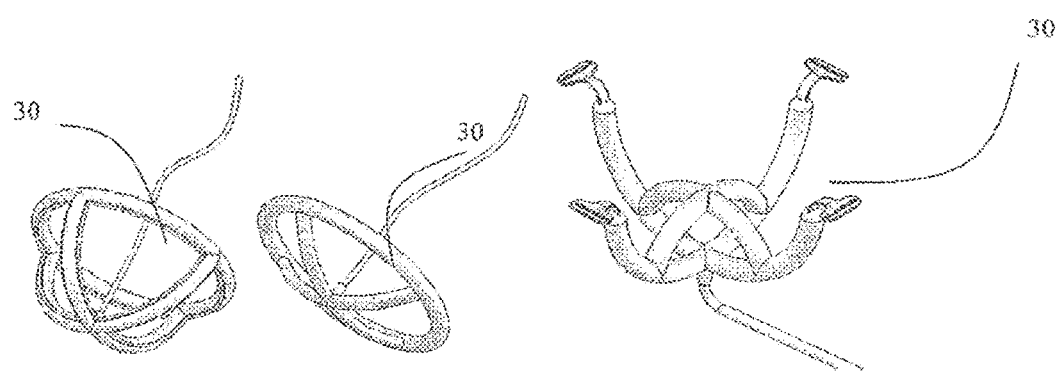

The inflatable contour-balloon 30 may have a flat structure as displays in FIGS. 13a, 13b, 13c, or a 3D structure as displays in FIGS. 13d, 13e and 13f.

Figures 13G, 13H:
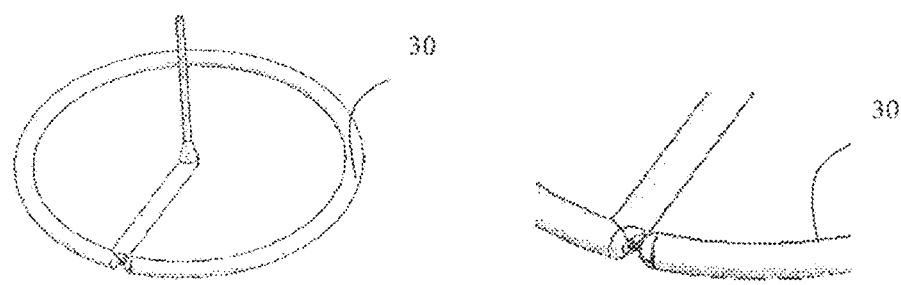

The inflatable contour-balloon 30 may not have a complete closed shape as can be seen in FIGS. 13g and 13h. The different parts of the inflatable balloon may be connected to each other with glue, wire, scotch Etc.

Figure 13I:
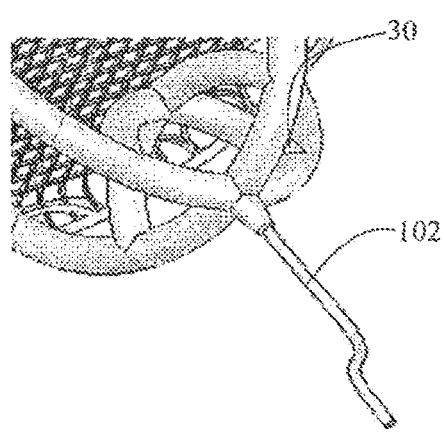
Figure 13J:
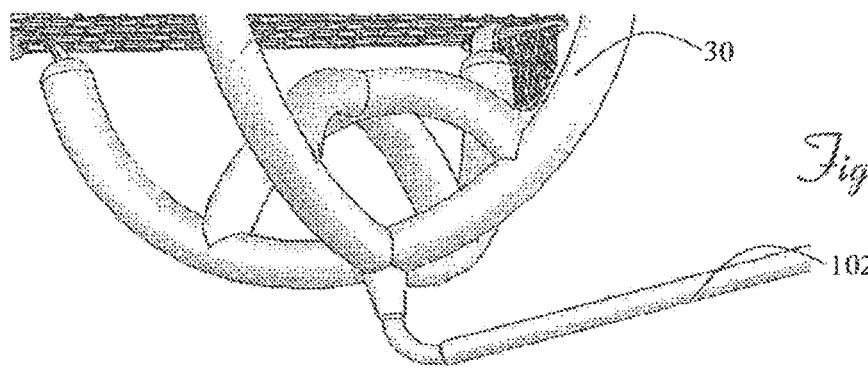
Figure 13K:
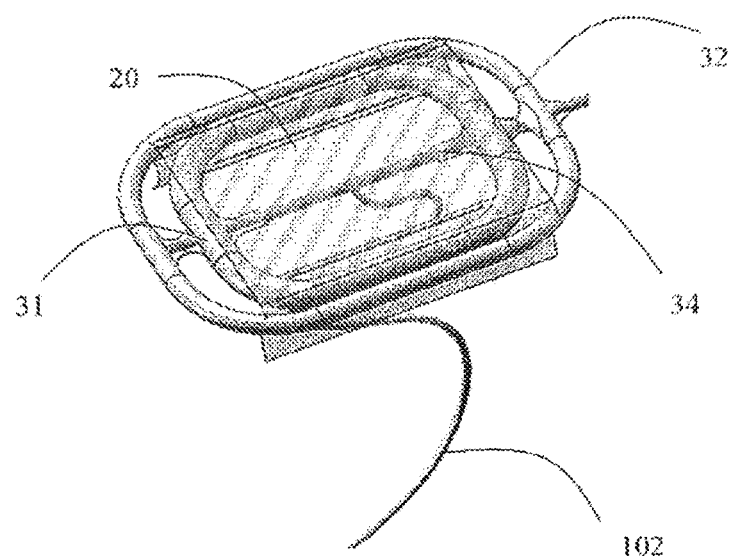
Figure 13L:
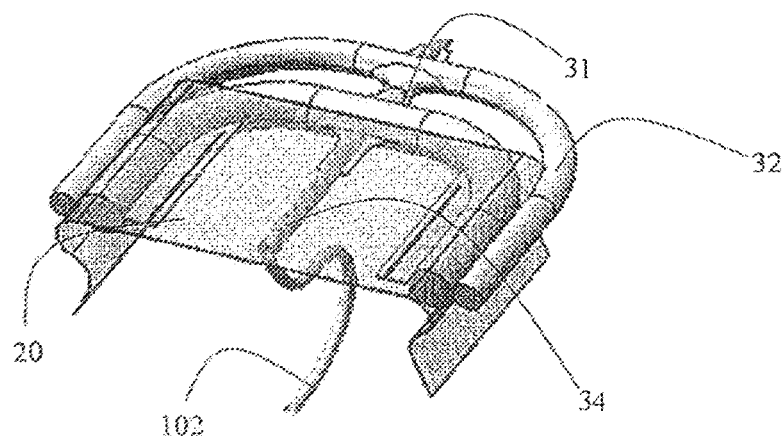

The inflating tube 102 may be flexible (FIG. 13i), or rigid (FIG. 13j). Moreover, the inflating tube 102 may not be connected to the center of the balloon 30. FIG. 13k represents a different design for the inflatable contour-balloon 30. According to this design, inflatable contour-balloon 30 has two parts. An internal pad 31 and an external part 32. Mesh 20 is positioned in between the internal part 31 and the external part 32. An inflating tube 102 is coupled to a tube 34, which passes through both the internal part 31 and the external part 32, FIG. 13I is a cross section area of the same.

In another embodiment of the invention the 2 balloons may be inflated with different pumps allowing the use of sequenced pumping.

Figure 13M:
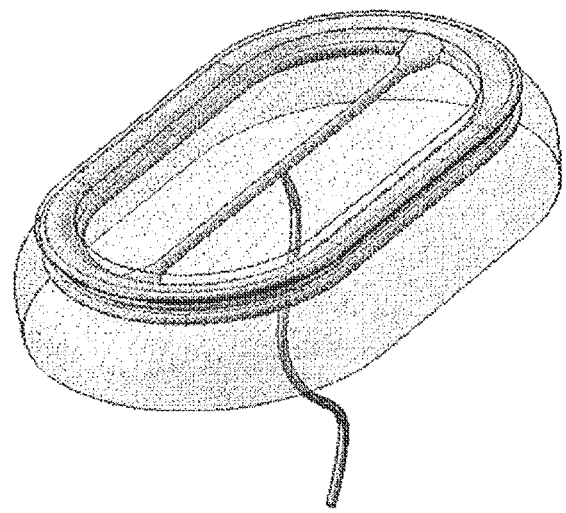
Figure 13N:
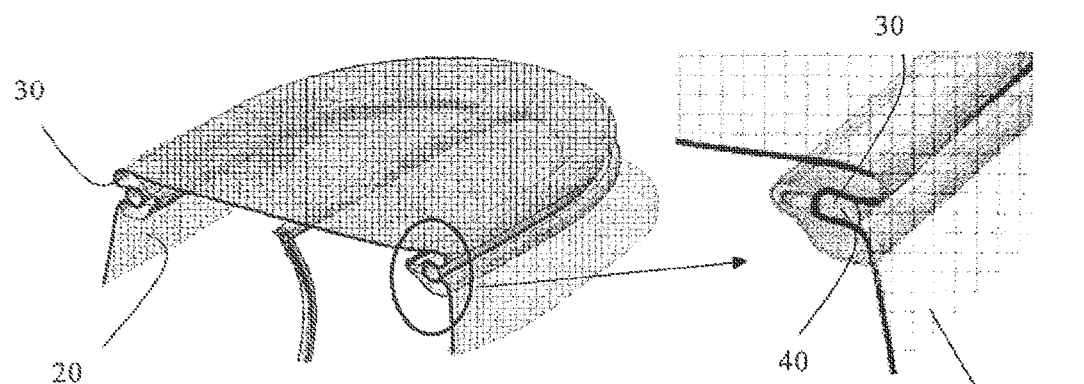
Figure 13O:
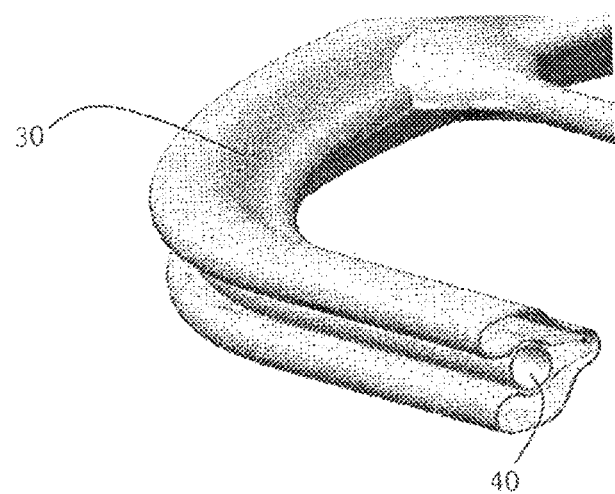

FIG. 13m represent another different design for the inflatable contour-balloon 30. According to this design, the inflatable contour-balloon 30 encapsulate an internal balloon 40 shaped as an o-ring. Mesh 20 is captured in between the inflatable contour-balloon 30 and the internal balloon 40. FIG. 13n is a cut and an enlarge view of the same. FIG. 13o displays the inflatable contour-balloon 30 and the internal balloon 40 according to this design.

Figure 14:
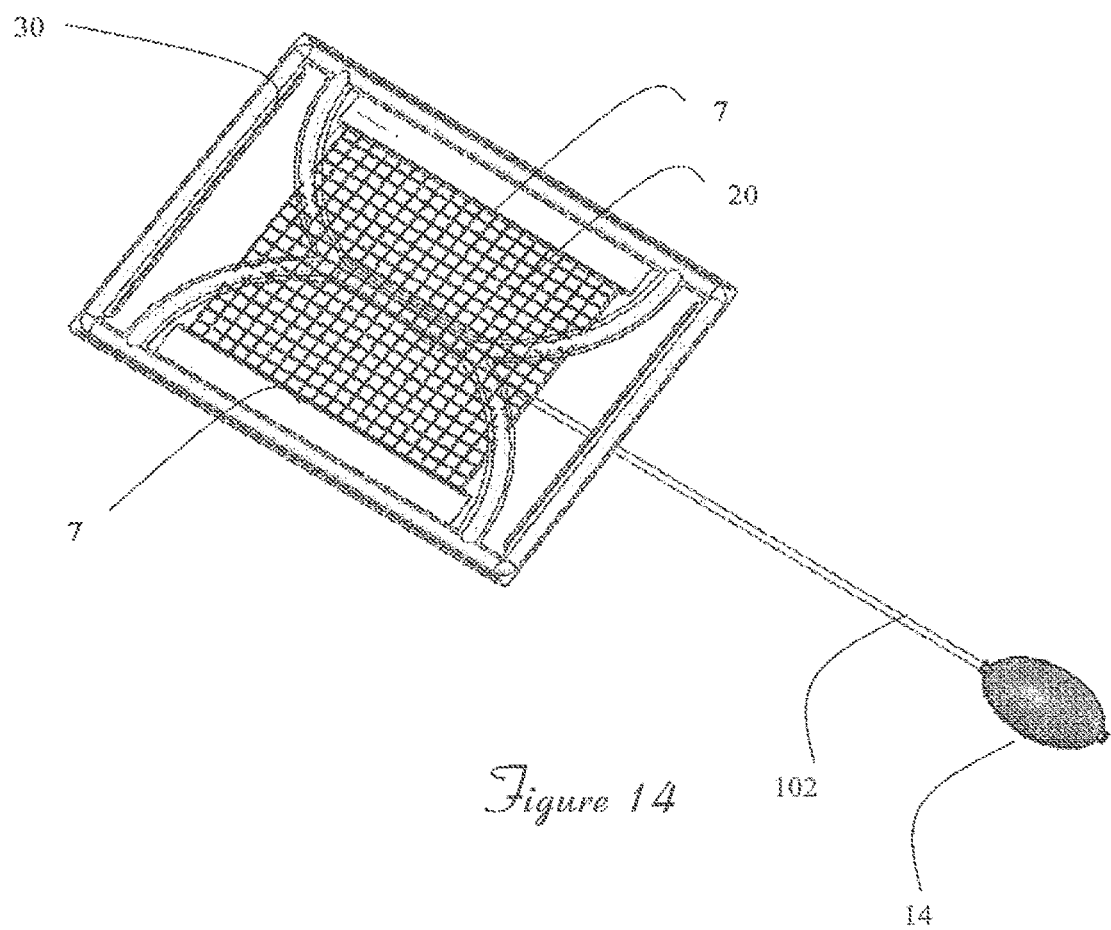
FIGS. 14, 15 and 16 schematically display different rectangle shapes of the inflatable contour-balloon and the mesh.
Figure 15:
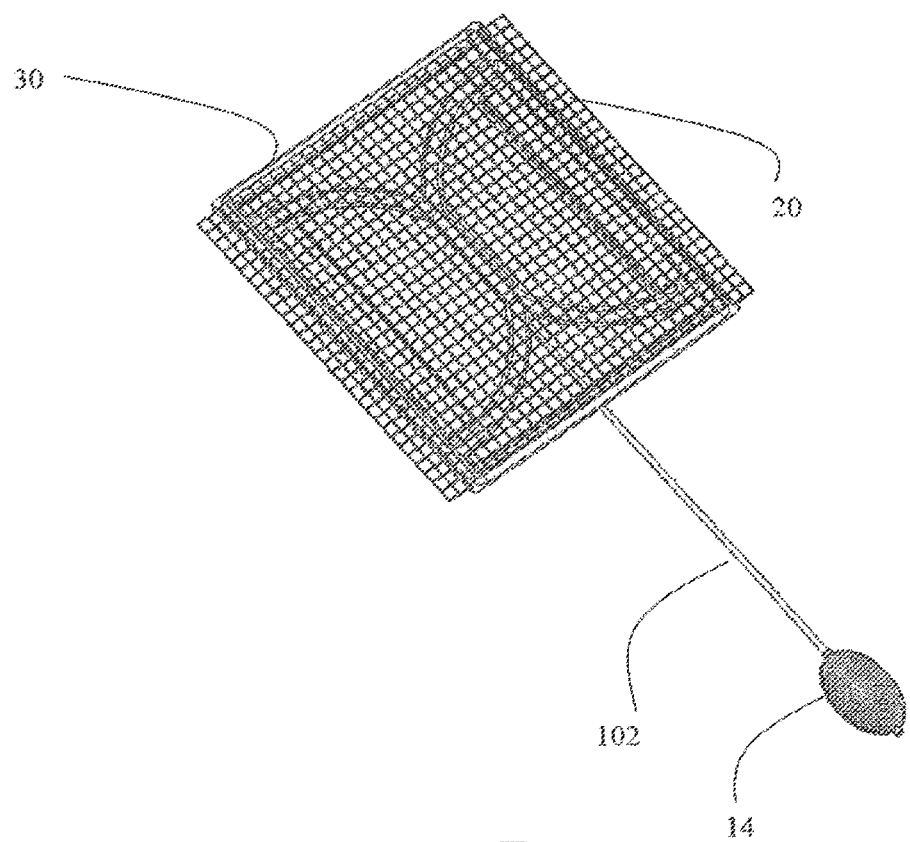
Figure 16:
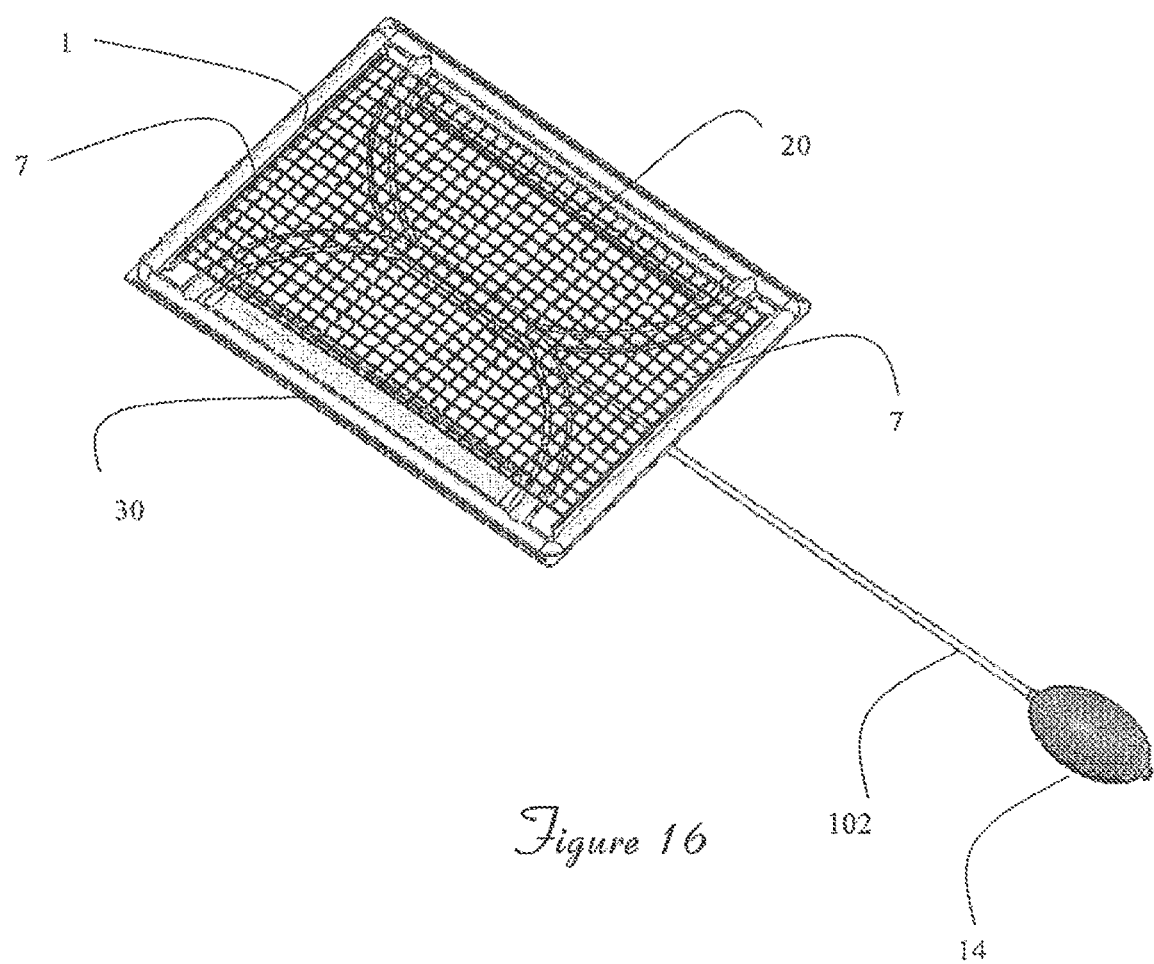

Reference is now made to FIGS. 14, 15 and 16, which schematically display different rectangle shapes of the inflatable contour-balloon 30 and mesh 20.

As can be seen from FIG. 14, the shape of the inflatable contour-balloon 30 is a rectangle shape having two oppositely faced curves. The two curves can be fused one to the other in a common section. Additionally, according to this embodiment mesh 20 is threaded in slits 7 which are positioned in two oppositely sides ribs on the rectangle.

Inflating tube 102 is connected to inflatable contour-balloon 30. An inflating pump 14 is connected to the inflating tube 102.

Reference is now made to FIG. 15, which schematically represents the inflatable contour-balloon 30 and the mesh 20 according to another embodiment of the present invention. According to this embodiment mesh 20 extends beyond the inflatable contour-balloon 30.

Reference is now made to FIG. 16, which schematically represents the inflatable contour-balloon 30 and the mesh 20 according to another embodiment of the present invention.

Figure 17:
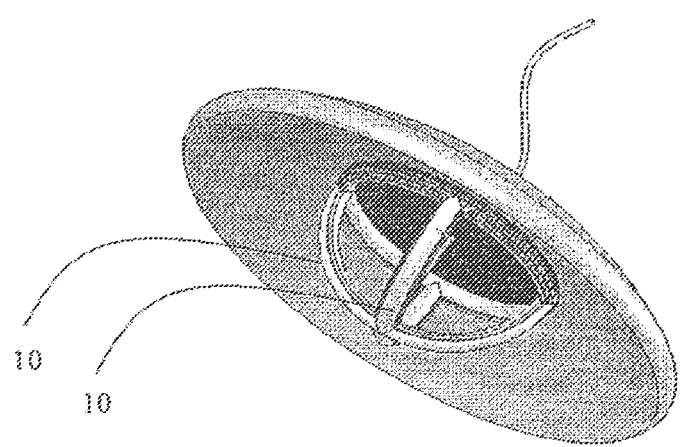
FIG. 17 schematically represents the inflatable contour-balloon and the mesh according to another embodiment of the present invention.

Reference is now made to FIG. 17, which schematically represents the inflatable contour-balloon 30 and mesh 20 according to another embodiment of the present invention. According to this embodiment, the inflatable contour-balloon 30 additionally comprises two arcs 10 that may replace the function of the dissection balloon. The inflatable contour-balloon 30 is fixed to its position, by creating pressure on the mesh/patch towards the abdominal wall.

Figure 18:
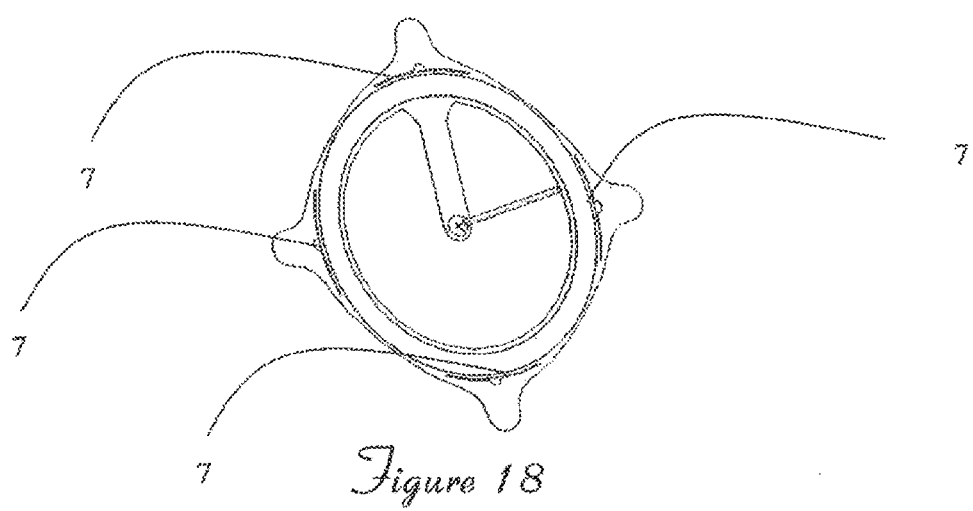
FIG. 18 displays an option of attaching the mesh to the inflatable contour-balloon.
Figure 19:
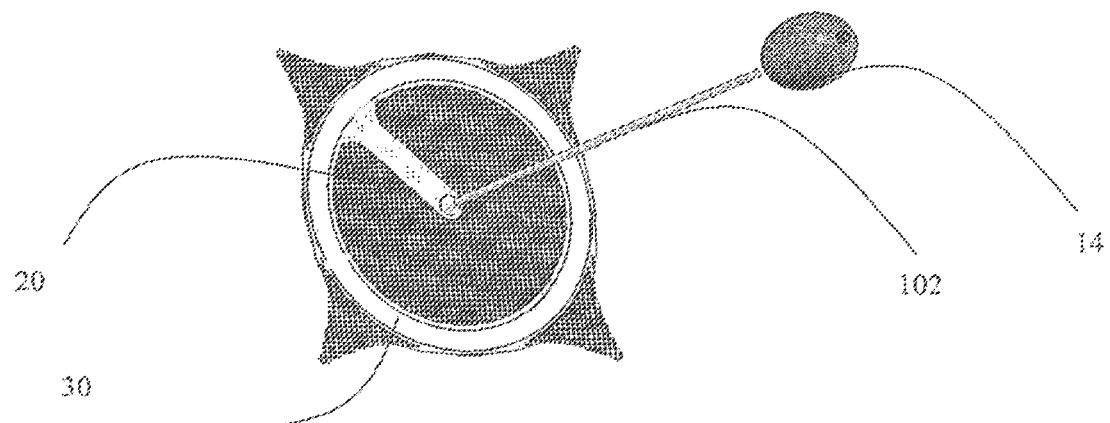
FIG. 19 displays the inflatable contour-balloon with the mesh threaded inside the slits.
Figure 20A:
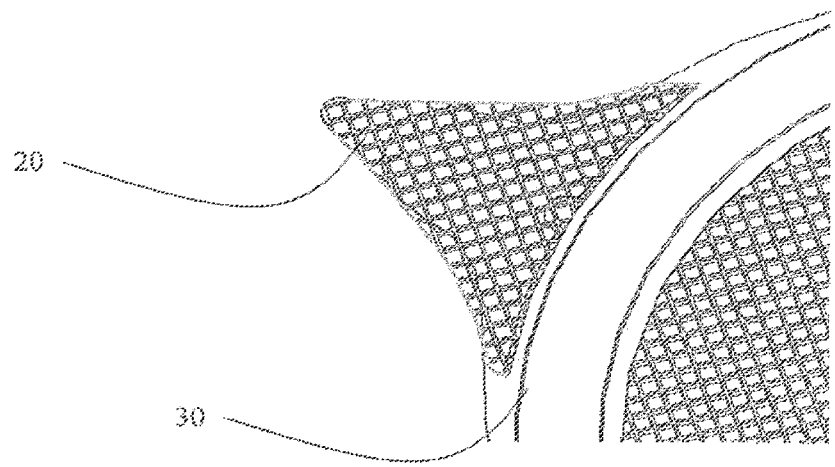

Reference is now made to FIG. 18, which displays an option of attaching mesh 20 to the inflatable contour-balloon 30. According to that embodiment, the inflatable contour-balloon 30 additionally comprises at least one slit 7 into which the edges of mesh 20 are threaded. FIG. 19 displays the inflatable contour-balloon 30 with mesh 20 threaded inside the slits. FIG. 20a and FIG. 20b display a more detail look of the same.

Another way of coupling between the inflatable contour-balloon 30 and the mesh is by making specials cuts in the mesh such that those cute surround the balloon as can be seen from FIGS. 20c and 20d.

Figure 20E:
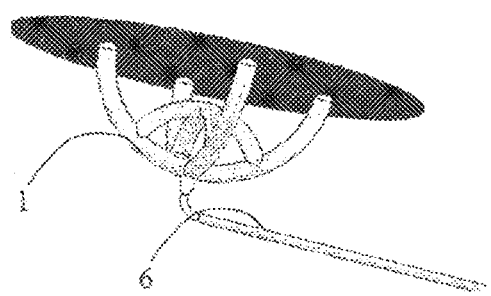
Figure 20F:
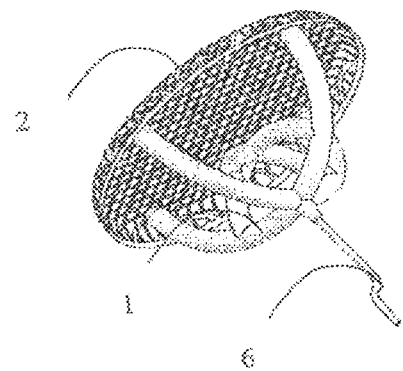
FIG. 20f displays another design of the inflatable contour-balloon and the mesh.

Another way to attach the inflatable contour-balloon 30 to the mesh is by double-sided adhesive material as displayed in FIG. 20e. FIG. 20f displays another design of the inflatable contour-balloon 30 and mesh 20.

Figure 20G:
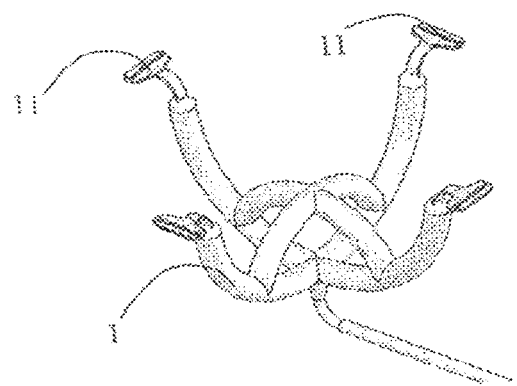
FIGS. 20g and 20h display another option to couple the inflatable contour-balloon and the mesh.
Figure 20H:
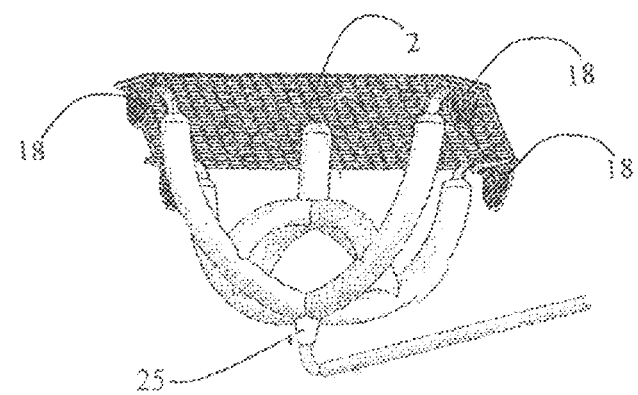

Another option to couple the inflatable contour-balloon 30 and mesh 20 is by using special extensions 11 as can be seen in FIGS. 20g and 20h. The special extensions 11 are insertable into extension 18 in the mesh 20. The inflatable contour-balloon 30 can additionally comprise means 25 (such as bulge, lines, signs and symbols) adapted to adjust the center of said inflatable balloon to the center of the hernia.

Figure 20I:
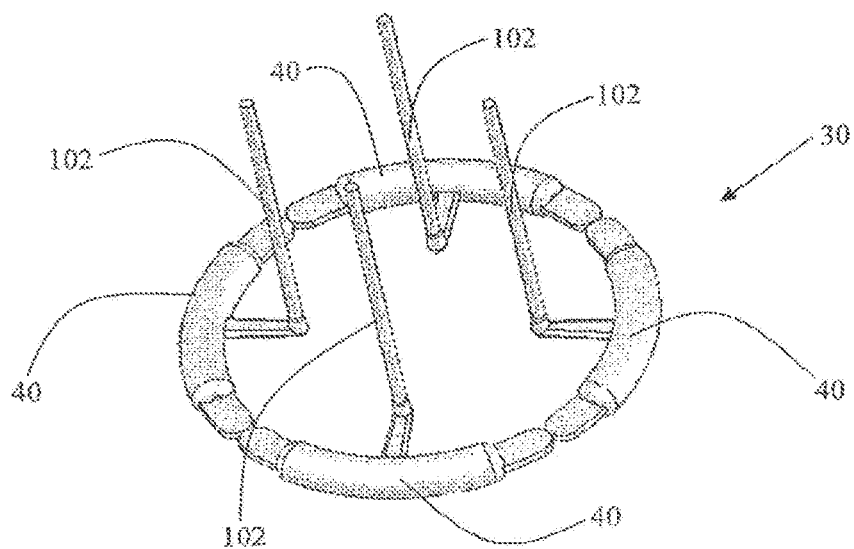
FIGS. 20i-20j display different designs of the inflatable contour-balloon.

Reference is now made to FIG. 20i, which schematically displays the inflatable contour-balloon 30, which comprises several independent parts 40 and several inflating tubes 102 (which will be couple to the inflating means). As can be seen from FIG. 20i tubes 102 are not positioned in the center of the balloon.

Figure 20J:
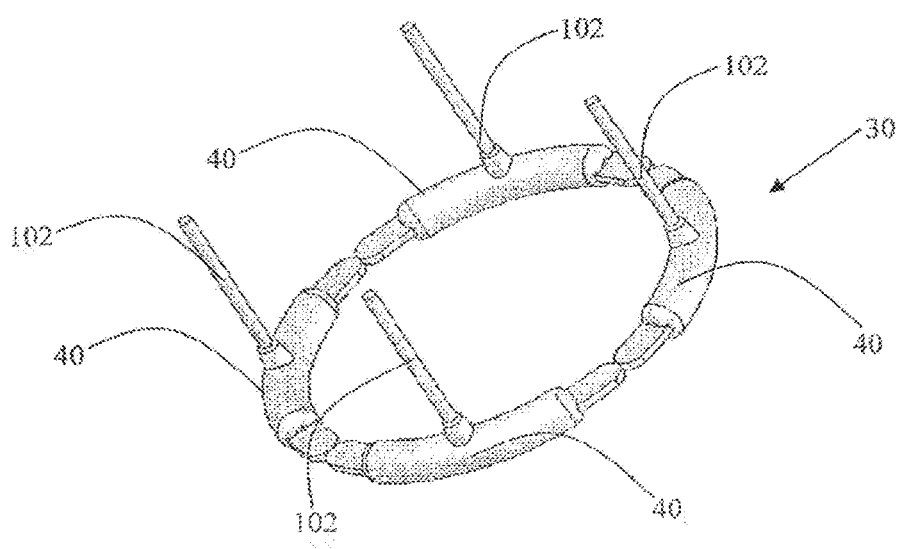

Reference is now made to FIG. 20j, which schematically displays the inflatable contour-balloon 30 comprising several independent parts 40 and several inflating tubes. As can be seen from FIG. 20i tubes 102 are not radial. I.e., tubes 102 are positioned in the perimeter of the inflatable balloon.

The invention claimed is:

1. A hernia repair device, comprising:
a mesh deployment device comprising an inflatable balloon comprising:
a first V-shaped expandable segment;
a second V-shaped expandable segment; and
an intermediate segment connecting the first V-shaped expandable segment to the second V-shaped expandable segment, wherein the intermediate segment extends from an apex of the first V-shaped expandable segment to an apex of the second V-shaped expandable segment, wherein the inflatable balloon has a flat structure, and wherein a concavity of the first V-shaped expandable segment and a concavity of the second V-shaped expandable segment face away from the intermediate segment.

2. The hernia repair device of claim 1, wherein the inflatable balloon further comprises:
a first expandable outer segment and a second expandable outer segment, the intermediate segment positioned between the first expandable outer segment and the second expandable outer segment.

3. The hernia repair device of claim 2, wherein the first expandable outer segment and the second expandable outer segment are at a perimeter of the inflatable balloon.

4. The hernia repair device of claim 2, further comprising a first opening and a second opening, the first opening being formed between the first expandable outer segment and the intermediate segment and the second opening being formed between the second expandable outer segment and the intermediate segment.

5. The hernia repair device according to claim 1, wherein the mesh deployment device further comprises an inflation tube.

6. The hernia repair device according to claim 1, further comprising a mesh coupled to the mesh deployment device.

7. The hernia repair device according to claim 6, wherein the mesh deployment device further comprises an inflation tube, and the inflation tube passes through the mesh.

8. The hernia repair device according to claim 6, wherein the mesh comprises a hernia repair mesh.

9. The hernia repair device according to claim 6, wherein the inflatable balloon has a top surface and a bottom surface situated on only one side of the mesh.

10. The hernia repair device according to claim 6, wherein the mesh extends beyond the inflatable balloon.

11. The hernia repair device according to claim 1, wherein the inflatable balloon is made of a shape memory material.

12. The hernia repair device according to claim 1, wherein the inflatable balloon has a substantially non-symmetrical shape.

13. The hernia repair device according to claim 1, wherein the intermediate segment is linear.

14. The hernia repair device according to claim 1, further comprising a first expandable end segment and a second expandable end segment, wherein the first V-shaped expandable segment is between the first expandable end segment and the intermediate segment, and the second V-shaped expandable segment is between the second expandable end segment and the intermediate segment.

15. The hernia repair device according to claim 14, wherein the first expandable end segment and the second expandable end segment are at a perimeter of the inflatable balloon.

16. The hernia repair device according to claim 14, further comprising a first opening and a second opening, the first opening being between the first expandable end segment and the first V-shaped expandable segment, and the second opening being between the second expandable end segment and the second V-shaped expandable segment.

17. The hernia repair device according to claim 14, wherein the first expandable end segment and the second expandable end segment are spaced from the intermediate segment.

18. The hernia repair device according to claim 1, wherein the concavity of the first V-shaped expandable segment faces away from the concavity of the second V-shaped expandable segment.

19. A hernia repair device, comprising:
a mesh deployment device comprising an inflatable balloon comprising:
a first V-shaped expandable segment;
a second V-shaped expandable segment; and
an intermediate segment connecting the first V-shaped expandable segment to the second V-shaped expandable segment, wherein the intermediate segment extends from an apex of the first V-shaped expandable segment to an apex of the second V-shaped expandable segment, wherein the inflatable balloon has a flat structure, and wherein a concavity of the first V-shaped expandable segment faces away from a concavity of the second V-shaped expandable segment.

20. A hernia repair device, comprising:
a mesh deployment device comprising an inflatable balloon comprising:
a first V-shaped expandable segment;
a second V-shaped expandable segment; and
an intermediate segment connecting the first V-shaped expandable segment to the second V-shaped expandable segment, wherein the intermediate segment extends from an apex of the first V-shaped expandable segment to an apex of the second V-shaped expandable segment, wherein the inflatable balloon has a flat structure, and wherein the intermediate segment is linear.

* * * * *

UNITED STATES PATENT AND TRADEMARK OFFICE
CERTIFICATE OF CORRECTION

PATENT NO. : 12,161,542 B2
APPLICATION NO. : 17/131505
DATED : December 10, 2024
INVENTOR(S) : Mordehai Sholev et al.

Page 1 of 1

It is certified that error appears in the above-identified patent and that said Letters Patent is hereby corrected as shown below:

In the Specification

At Column 9, Line 42, "wan" is deleted and -- wall -- is inserted

At Column 10, Line 5, "zine" is deleted and -- zinc -- is inserted

At Column 10, Line 33, "lit" is deleted and -- fit -- is inserted

At Column 11, Line 32, the second occurrence of "30" is deleted and -- 20 -- is inserted At Column 13, Line 56, "10$e$" is deleted and -- 10$c$ -- is inserted At Column 14, Line 43, "pad" is deleted and -- part -- is inserted Signed and Sealed this
Fourth Day of February, 2025

Coke Morgan Stewart
*Acting Director of the United States Patent and Trademark Office*